(12) United States Patent
Chenchik

(10) Patent No.: US 9,447,411 B2
(45) Date of Patent: Sep. 20, 2016

(54) METHODS AND COMPOSITIONS FOR SINGLE CELL EXPRESSION PROFILING

(71) Applicant: CELLECTA, INC., Mountain View, CA (US)

(72) Inventor: Alex Chenchik, Redwood City, CA (US)

(73) Assignee: Cellecta, Inc., Mountain View, CA (US)

( * ) Notice: Subject to any disclaimer, the term of this patent is extended or adjusted under 35 U.S.C. 154(b) by 0 days.

(21) Appl. No.: 14/153,864

(22) Filed: Jan. 13, 2014

(65) Prior Publication Data

US 2014/0206546 A1 Jul. 24, 2014

Related U.S. Application Data

(60) Provisional application No. 61/752,233, filed on Jan. 14, 2013.

(51) Int. Cl.
*C12N 15/10* (2006.01)
*C40B 50/06* (2006.01)
*C12Q 1/68* (2006.01)

(52) U.S. Cl.
CPC ......... *C12N 15/1072* (2013.01); *C12N 15/102* (2013.01); *C12N 15/1065* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 2004/0048311 A1 | 3/2004 | Ault-Riche et al. | |
| 2004/0058344 A1 | 3/2004 | Mitchell et al. | |
| 2004/0220127 A1 | 11/2004 | Sternberg et al. | |
| 2005/0186597 A1* | 8/2005 | Michels | 435/6 |
| 2006/0154257 A1* | 7/2006 | Mitchell | C12N 15/1027 435/6.14 |
| 2007/0059726 A1 | 3/2007 | Cao | |
| 2007/0202505 A1 | 8/2007 | Chenchik | |
| 2008/0096255 A1 | 4/2008 | Harbers et al. | |

(Continued)

FOREIGN PATENT DOCUMENTS

| | | |
|---|---|---|
| WO | WO 00/09734 A2 | 2/2000 |
| WO | WO03104412 | 12/2003 |

(Continued)

OTHER PUBLICATIONS

Islam et al (2011) "Characterization of the single-cell transcriptional landscape by highly multiplex RNA-seq" Genome Research 21:1160-1167.*

(Continued)

*Primary Examiner* — Karen S Weiler
(74) *Attorney, Agent, or Firm* — Bret E. Field; Bozicevic, Field & Francis LLP

(57) ABSTRACT

Methods of obtaining a single cell expression profile from a target mammalian cell are provided. Aspects of the methods include contacting a cellular sample which includes the target mammalian cell with a packaged viral barcoded trans-splicing library including a plurality of barcoded trans-splicing constructs under transduction conditions, where a barcoded trans-splicing construct includes a trans-splicing element linked to a barcode element. The methods further include generating expression data from the resultant transduced target mammalian cell to obtain the single cell expression data from the target mammalian cell. Also provided are compositions, e.g., libraries and components thereof, which find use in practicing the methods.

20 Claims, 14 Drawing Sheets

(56) References Cited

U.S. PATENT DOCUMENTS

| | | |
|---|---|---|
| 2008/0166758 A1 | 7/2008 | Engelhardt et al. |
| 2010/0305002 A1 | 12/2010 | Chenchik et al. |
| 2011/0160078 A1 | 6/2011 | Fodor et al. |

FOREIGN PATENT DOCUMENTS

| | | |
|---|---|---|
| WO | WO 2005/026378 A2 | 3/2005 |
| WO | WO 2007/126882 A2 | 11/2007 |
| WO | WO 2010/129310 A1 | 11/2010 |

OTHER PUBLICATIONS

Lu et al (2011) "Tracking single hematopoietic stem cells in vivo using high-throughput sequencing in conjunction with viral genetic barcoding" Nature Biotechnology 29(10):928-934.*

Gallegos (2011) "The role of the Ou element in SL1 trans-splicing in C. elegans nematodes" Undergraduate Honors Theses, University of Colorado Boulder, Paper 596. downloaded from : http://scholar.colorado.edu/cgi/viewcontent.cgi?article=1791&context=honr_theses.*

Shendure et al. (2008) "Next-generation DNA sequencing" Nature Biotechnology 26(10):1135-1145.*

Mansfield et al. (2003) "5' exon replacement and repair by spliceosome-mediated RNA trans-splicing." RNA 9(10):1290-1297.*

Sarkis et al. (2008) "Non-Integrating Lentiviral Vectors" Current Gene Therapy 8(6):430-437.*

Arad (1998) "Modified Hirt Procedure for Rapid Purification of Extrachromosomal DNA from Mammalian Cells" BioTechniques 24:760-762.*

ABM Inc. "Knowledgebase: Cell Culture—Adenovirus Techniques" https://www.abmgood.com/marketing/knowledge_base/cell_culture_adenovirus_techniques.php, captured May 19, 2016.*

Ormondt et al (1984) "Nucleotide Sequences of Adenovirus DNAs" Curr Top Microbiol Immunol vol. 110, p. 73-142.*

Bernards et al., "shRNA libraries and their use in cancer genetics", Nature Methods, vol. 3, No. 9, pp. 701-706 (2006).

Boettcher et al., "Decoding pooled RNAi screens by means of barcode tiling arrays", BMC Genomics, vol. 11, Article No. 7, pp. 1-16 (2010).

Cellular Research Inc.—Technology Whitepaper, "Pixel System™", White Paper, pp. 1-12 (2014).

http://www.cellecta.conn ("CELLECTA" Webpage) Mar. 2012 (tracked by online Wayback Machine) See Products Services page(RNAi genetic screens), and Technology page (shRNA library construction, and RNAi genetic screening.

Fewell et al., "Vector-based RNAi approaches for stable, inducible and genome-wide screens", Drug Discovery Today, vol. 11, Nos. 21/22, pp. 975-982 (2006).

Gerrits et al., "Cellular barcoding tool for clonal analysis in the hematopoietic system", BLOOD, vol. 115, No. 13, pp. 2610-2618 (2010).

Gresham et al., "System-Level Analysis of Genes and Functions Affecting Survival During Nutrient Starvation in *Saccharomyces cerevisiae*", Genetics, vol. 187, pp. 299-317 (2011).

Hamady et al., "Error-correcting barcoded primers for pyrosequencing hundreds of samples in multiplex", Nature Methods, vol. 5, No. 3, pp. 235-237 (2008).

Hug et al., "Measurement of the Number of Molecules of a Single mRNA Species in a Complex mRNA Preparation", Journal of Theoretical Biology, vol. 221, No. 4, pp. 615-624 (2003).

Mazurkiewicz et al., "Signature-tagged mutagenesis: barcoding mutants for genome-wide screens", Genetics, vol. 7, pp. 929-939 (2006).

Nolan-Stevaux et al., "Measurement of Cancer Cell Growth Heterogeneity through Lentiviral Barcoding Identifies Clonal Dominance as a Characteristic of In Vivo Tumor Engraftment", PLOS ONE, vol. 8, No. 6, pp. e67316-e67316 (2013).

Pierce et al, "Genome-wide analysis of barcoded *Saccharomyces cerevisiae* gene-deletion mutants in pooled cultures", Nature Protocols, vol. 2, No. 11, pp. 2958-2974 (2007).

Shtutman et al., "Function-based gene identification using enzymatically generated normalized shRNA library and massive parallel sequencing", PNAS, vol. 107, No. 16, pp. 7377-7382 (2010).

Sims et al., "High-throughput RNA interference screening using pooled shRNA libraries and next generation sequencing", Genome Biology, vol. 12, Article No. R104, pp. 1-13 (2011).

Smith et al., "Competitive Genomic Screens of Barcoded Yeast Libraries", Journal of Visualized Experiments, vol. 54, No. e2864, pp. 1-7 (2011).

Warner et al., "Rapid profiling of a microbial genome using mixtures of barcoded oligonucleotides", Nature Biotechnology, vol. 28, No. 8, pp. 856-862 (2010).

Kim, et al. "Mammalian cell transfection: the present and the future", Anal Bioanal Chem. Aug. 2010; 397(8): 3173-3178.

Hashimshony, et al. "CEL-Seq: single-cell RNA-Seq by multiplexed linear amplification" Cell Rep. Sep. 27, 2012;2 (3):666-73.

Ramsköld, et al. "Full-length mRNA-Seq from single-cell levels of RNA and individual circulating tumor cells", Nat Biotechnol. Aug. 2012;30(8):777-82.

Zador, et al. "Sequencing the Connectome", PLoS Biol., Oct. 2012; 10(10): e1001411.

Communication—The extended European search report for European Patent Application No. 14737887.1, mailed on Jun. 22, 2016, 9 pages.

* cited by examiner

BstBI    CMV promoter
ACTAGTATTATGCCCAGTACATGACCTTATGGGACTTTCCTACTTGGCAGTACATCATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAATGGGAGTTTGTTTTGGCACCAAAATCAACGGGACTTTCCAAAATGTCGT
AACAACTCCGCCCCATTGACGCAAATGGGCGGTAGGCGTGTACGGTGGGAGGTCTATATAAGCAGAGCTGGTTTAGTGAACCGTCAGATCGCCTGGAGACGCCATCCAC
GCTGTTTGACCTCCATAGAAGACACCGGGGACCGCTAGCGCTAGAGATCTGGTACCGTCGACTGCAGGAATTCGATATCAAGCTTATCGATACCGTCGACCTCGAG
GCTGTTTGACCTCCATAGAAGATCTAGAACACAGCCTAGCGCTAGAGACGCCACCATGGTGTCT
                              Xba I      Nhe I        +1  tagRFP

B

Xba I       BP           PPT       SA
TCTAGAGACCGTACTGACCCGTCTGTTCCTTTTTTTCACAGTTCCTGAGGACTGTGGAACCTCTGAACTCTGAGGACTGTGAACTCTGAAGA
AGATCTGGAGGAGAGGACAAAGGAAAAAAAAGTGTCAAGGACTGAGACTCTTGGAAAATCTGAGGACTGTATATTCTGTCGTCTCGGTGGTCG
AGATCTGGAGGAGAGGACAAAGGAAAAGA        AGAGCCACCAGCGGGCATAGTAA      AAGACAGCAGCCACCA
           GexSeq5                        Gex2M                       RF9
                                                                              Nhe I

C

5' CAP ATCGCCTGGAGACGCCACCATCCAGCTGTTTGACCTCCATAGAAGATCTAGAACACAGCCTAGCGCTAGAGACCCTCCTCTGTTCCTTTTTTTCACAGTTCCTGACTGT
AACTCTGAACCTCTCCTTGCGTGTAAGGTCGTCTCGGTGTAGGCGCCGTATCATTCATTCTGTCGCTAGCTAGCGGTCGTCCGTAGCTAGACGCCACCATGGTGTCT
                 Xba I      BP              PPT         SA
                                                                   Nhe I    tagRFP

```
XbaI +1           BP              PPT      SA                    ESE1
TCTAGATCGCCTGGAGACGGCCATCCACGCCTGTCTCTGACCCTTGTTCTTTTTCTGTGGAGAGTTGACGTCGGAGAAGAAGCTGTCATTTCAGTGTGGAATGGTGTC
TCCAGGTGATACGGGACTCTTCTGAAGACACTTCGTCTGCGGTCGTCTGCGGTTGTCTCCGGTCCGTCGGTCTCGGGTCTCGCTAGC
        BpiI    BpiI                                                                  NheI
```

E

```
            HstBI
TTGAATTAACGGAGTACATGACGTTAGGGACTTTCCTACGTTGGCAGTACATCTAAGCTATTAGTCATTGACCTCGTTGCCGTTTTGGCAGTACATCAAT
GGGCGTGGATAGCGGGTTTGACTCGACGGGGATTTCCAAGTCTCCACCCCAATGGGAGTTTGTTTGGTCACCGAAATCAAGGGACTTTCCAAAATGTCGTA
ACAACTCCGCGCCCATTGACGCAATGGGCGGTGGCGGTGTACGGTGGAAGGTTTATATAAGCAGAGCTCGTTTAGTGAACCTCTAGATTTTGCTAGCTAGCCAGACGC
CACCATGGTGTCT                                                                  XbaI +1       NheI
                                                                                 Bpi    Bpi
```

F

```
XbaI +1       BP        PPT        SA          ESE5                              Bpi      Bpi
TCTAGATCGTACTGACTCTGTTTCTTTTTTCTGCAAGAGTTGACAGTTGACGTCGGGAGAAGAAGCTGTTCAATACCGGAGTCTTCTTATTAGAAGACACTTCGTCTGCCGTTGTT
CTCGGGTGGTCGGTCGCCGTTCTCGTGTCGGGTCGCTAGC
                                 NheI
```

```
XbaI +1           BP         PPT           SA                              ESE5                Bpil
TCTAGATTCCCGGGAGACACTCCGGGAATTTCTGACCTTGTTTCTTTTTTCTGCAGACCGATCCTGCTGAACAAGACGACTGGTCTGCTTACCGGAGTCTTCTT
GAAGACACTTCGTCTGCGTTGTCTCGGTGGTCGGCCGTTCTCGTGCGTGGGTGCTCGCTAGC
     BpiI                                                             NheI
```

H

```
XbaI +1           BP         PPT           SA                              ESE5                Bpil
TCTAGATTCCCGGGAGACACTCCGGGAATTTCTGACCTTGTTTCTTTTTTCTGCAGACCGATCCTGCTGAACAAGACGACTGGTCTGCTTACCGGAGTCTTCTT
GAAGACACTCTGCGTTGTCTCGGTGGTCGCCGTTGTCTCGTCGTTGTCGGTGCTCGATCAGGTAAGTGCTAGC
     BpiI                                                          SD    NheI
```

I

```
XbaI +1           BP         PPT           SA                              ESE5                Bpil
TCTAGATTCCCGGGAGACACTCCGGGAATTTCTGACCTTGTTTCTTTTTTCTGCAGACCGATCCTGCTGAACAAGACGACTGGTCTGCTTACCGGAGTCTTCTT
GAAGACACCAGGTAAGTCTAGCTTGCGTTGTTCTCGGTGTCGCCGTTCTGTTCGTGTTCGGTGCTCGKTAGC
         SD                                                               NheI
```

```
Xba1 +1                BP              PPT              SA                              KSE5
TCTAGATTCCGGAGACACACTCCGGGAATTTCTGACCTTGTTCTTTTTTTTCTGCAGACCGATCCTGCTGAACAAGAGACTCGTGCTGAACAGAGTCGTT
GAAGACACTCCTGCGTTCTCGGTCTGCGGTGTCCGGTCTCTGCCGTCGGTGTCCCGTTGCGATCAGTTCATATAACCATCTACTAACCGTCCCCTGTTCTTCTTCACAG
GTTGCTAGC                                             SD       BP                    PPT       SA
    NheI
```

K

```
Xba1 +1    Hairpin         BP             PPT        SA            KSE5
TCTAGATTCCGGAGACACACTCCGGGAATTTCTGACTTGTCTTTTTTTTCTGCAGACCGATCCTGCTGAACAAGAGACTCGTGCTT
ACAACTAGGGCCTTGTGTGAGGCCTTGTCTGTGTGTTGTCTGAGACTGAAACAAGAAAAAAAAGAAGCTCAGCTCAGAGACTCGTTCTGCTGAAGCAGAAGGAA
                                                      TGGCTAGGACGACTTGTTCTGCT SeqTMP18
                                                                                      NheI
```

```
    CB18H
ACCGRHHHHHHHHHHHHHHHH TCGTCCTGGGTTGTTCTGCGGGTCCTGCCGTTGTTCGTCGTTCGGGTGCTCGCTAGC
TGGCCDDDDDDDDDDDDDDDN AAGCAGAAGAGACCACCAGCAACAGCCACCAGCAACAGCAGCCACGACGATCG
```

L

```
5'RSV/LTR-ClaI-EcoRI-XhoI-bGHpA-BstBI-CMV-XbaI-BpiI/BpiI-Acc65-3'dLTR
                  ClaI  EcoRI  XhoI   bGHpolyA
ATTAGTGAACGGATCGATCTCGGAATTCGAATTCGAATTCTCCTCGAGTTTTGCCCCTCCCCGTGCCTTCCCCTTGACCC
TGGAAGGTGCCACTCCCACTGTCCTTTCCACTGATAAAATGAGGAAATTGCATCGCATTGTCTGAATAGGTGTCATTCTATTC
                BstBI      CMV promoter
TGGGGGGTGGGGTGGGGGCAATTCGAATTAACCGCAGTACATGACCGTTATGGGGACTTTCCTACTTCGCAGTACATCTACGTAT
TAGTCATCGCTATTACCATGCAGATACGGTTTTCGCAGTACATCAATGGGGCGTGATAGCGCTTTGACTCACGGGGATTTC
CAAGTCTCCACCCCATTGACCGCCAATGGAGTTTGTTTTGGCACCAAATCAACGGGACTTTTCCAAATGTCGTAACAACT
CCGGCCCATTGACGCAAATGGGCGCTAGGGGCGTAGGCGGAAGGTCTATATAAGCAGAGCTCGTTTAGTGAACCTCTAGA
                                                                                BstBI
    BpiI  BpiI  Acc65
TTCGAGTCTTCTGTTTGAAGACACTTCGAAGGTACCTTTAAGACCAAATGACTTTAACAAGGCAGCTGTAGATCTTAGCCACTTT
    BpiI
```

5'RSV/LTR-ClaI-EcoRI-cPPT-XhoI-bGHpA-U7Promoter-BpiI/BpiI-U7snRNA-EcoRI-Acc65-
3'dLTR
ClaI          EcoRI            cPPT
ATCGATCTTTTTGTCGAATTCTTTTTAAAAGAATTACAAAACAAATTACAAAAATTCAAAAATGGGGGGTACAGTGCAGGGGAAAGAATAGTAGACATA
ATAGCAACAGACATACAAACTAAGAATTACAAAACAAATTACAAAAATTCAAAAATTTTCTCGAGTTTTGCCCCTCCCC
                                                          XhoI    bGHpolyA
CGTGCCCTTCCTTGACCCTGGAAGGTGCCACTCCCACTGTCCTTCCTAATAAAATGAGGAAATTGCATCGCATTGTCTGAA
                                                              U7 promoter
TAGGTGTCATTCTATTCTGGGGGGTGGGGTGGGGCAATCGAATCGATCCCACATCGCTTGCCACTACTAAGTCCGATTCA
CTTCGGGCTTTAGTCCCAAGCCTTTAATCTCGCGAAGCTCTTTTTTTTTTAACAACATAGGAGCTGTGATTGGCTGTTT
TCAGCCAATCAGCACTGACTCATTTGCATAGCCTTTACAAGCGGTCACAAACTCAAGAACGAGGGGTTTTAATAGTCTT
TAGAATATTGTTTATCGAACGAATAAGGAACTGTGCTTTGTGATTCACATATCAGTGGAGGGGTGTGAAATGGCACCTT
                                                                  BpiI    BpiI
GATCTCACCCCTCATCGCGAAAGTGGAGGAGTTGATGTCCTTCCGCCTACAGAGACGCACTTCCGCAAGAGTCTCTTATGAA
    U7 snRNA
GACTCCTTCGTAATTTTTGGAGCAGGTTTTCTGACTTCGGTCGGAACTTCACTGGTCTACAATGAAAGCA
AAACAGTTCTCTTCCCCGCTCCCCGGTGTGTGAGAGGGCTTTGATCCTTCCTGGTTTCCTAGGAAACGCGTATGTGCTA
GAGCCACGCTCTGAGACTTCCGCCCTTCCTTTCTGCCCTCCTCCTCTGGGAATTCGGTACCTTTAAGACCAA

Xhol-ldITR-ClaI-EcoRI-XhoI-bGHpA-BstBI-CMV-XbaI-BpiI/BpiI-Acc65-NotI-SV40polyA-
SpeI-rITR-F-PstI
     XhoI                    L-dITR
ATTACGCCAAGCTCTCGAGGGCCACTCCCTCTCGCGGCTCGCTGAGGCCGGGGCGACCAAAGGTCGCCCGAC
   SmaI    XhoI                                                       
GCCCGGGCTTTGCCCGGGCGGCCTCAGTGAGCGAGCGCGCAGAGAGGGAGTGGCCAACTTCCATCACTAGGGGTTCCT
                         ClaI    EcoRI    XhoI                     bGHpolyA
GGGAGGGGTGGAGTCGGTGAATCGGATGTCCGAATTCTCCCTCGAGTTTGCCCCTCCCCGTGCCTTCCTTGACCCTGGAAGGT
GCCACTCCCACTGTCCTCTTTCCTAATAAAATGAGGAAATTGCATCGCATTGTCTGAGTAGGTGTCATTCTATTCTGGGGGGT
     BstBI                          CMV promoter
GGGGTGGGGCAGGACAGCAAGGGGGAGGATTGGGAAGACAATAGCAGGCATGCTGGGGATGCGGTGGGCTCTATGGGCTTCT
                     Acc65    NotI
TTGACGCAAATGGGCGCTAGGCGTGTACGGTGGAAGGTCTATATAAGCAGAGCTCGTTTAGTGAACCTCTAGATTCGAGTC
                                                                          XbaI
GCTATTACCATGCAGATGCAGTTTTCGCAGTACATCAATGGCGTGATAGCGCTTTGACTCACGGGGATTTCCAAGTCTC
CACCCCATTGACGCAAATGGCCAATTGGGAGTTTGTTTTGGCACCGAATCAACGGGACTTTCCAAAATGTCGTAACAACTCCGCCCA
     BpiI    BpiI                                                         XbaI
TTCTTTTGAAGACACTTCGAAGTAACGGTACCGCGGCCGCTAAGGCCTAAGTCCGATCTGCGATCTCGAATTCCACCTGCCTGAGATCATGACATGGTTTGTGAAATTTGTGA
TGCTATTGCTTTATTTGTAAACACTTTAAACACTTTAAACACTGCAATAAGAATCAAATGGCGCCGCGGATCCGGAGTGGAGCTGGAGCTAGAGCTACGA
AATAAACACTTTAAACACTTTAAACACTTTAAACACTGATTAACGAAATAAACATTGGTAATAATATTCGACGTTATTGTTTGTTAACAACAACAATTGCA
                         SpeI                                   L-ITR
TTCATTTTATGTTTCAGGTTCAGGGGGAGGTGTGGGAGGTTTTTAAACTAGTCCACTCCCTCTCTGCGCGCTCGCTCGCT
                     SmaI    SmaI
CACTGAGGCCGGGCGACCAAAGGTCGCCCGACGCCCGGGCTTTGCCCGGGCCCTCAGTGAGCGAGCGAGCGCGCAGAGA
PstI
GGGACTGCAGAATACTCTCGACAATTCACTGGCCGTCGTTTTACAACGTCGTGACTGGGAAAACCCTGGCGTTACCCAACT

LdITR-F-ClaI-EcoRI-XhoI-bGHpA-BstBI-bGHpA-U7Promoter-BpiI/BpiI-U7snRNA-EcoRI-
Acc65-NotI-SV40polyA-SpeI-rITR-F-PstI

```
                Xho I                L-dITR-F
ATTACGCCAAGCTCTCGAGGCTCCTCCCTCTCTGCGGCTCGCTGCTCACTGAGGCCGGGCCGACCAAAGTTCGCCCGAC
        SmaI                                                          trs
GCCCGGGGCTTTGCCCGGCGACCTCAGTGAGCGAGCGAGCGCGCAGAGAGGGAGTGGCCAACTCCATCACTAGGGGTTCCT
                                                                                BstBI
GGAGGGGGTGGAGTGTGAATCGATTTTTGCCCCTCCCCGTGCCTTCCTTGACCCTGGAAGGTGCCACTCCCACTGTCCTT
                       ClaI
TCCTAATAAAATGAGGAAATGCATCGCATTGTCTGAATAGGTGTCATTCTATTCTGGGGGGTGGGGTGGGGCAATCGAAT
CGATCCCACATCGCCCTGCCAATTCACTTCACTGATCCAGCTTAGCTCGGCTTTTTCCAAGCTCTATAGCCTTTACAAGG
TTTTTTTTTAACAACATAGAGAGTGTGATTGGCTGTGTTTTAGAAATATTGTTTTATCGAACCGAATAAGGAACTGTGTTTGTG
GTCACAAACTCAAGAAACGAGCGGGTGTGAAGAGTCCACCTTGATCTCACCCTCATCGAAAGTGGAGTGATGTCCTTCCCTGGC
ATTCACATATCAGTCAGTGGAGGGGTGTGAAGAGTCCTCTTATGAAGACTCTTCGTAATTTTTCCCCGGTCGG
               BpiI   BpiI
TCGCTACAGACGGCACTTCCGCAAGAGTCCTCTTATGAAGACTCTTCGTAATTTTTCCCCGGTGTGAGAGGGGCTTT
AAAACCCCTCCAATTCACTGGTCCTACAATGAAAGCCAAAACAGTTCTCTTCCCCGGTGTGAGAGGGGCTTT
GATCCTTCTCTGGTTCCTAGGAAACGCGTATGTGCTAGAGCCACCGTAGCCTTCCGCGCTCTGAGACTTCCGCGGTCCCGGTTCCT
     EcoRI Acc65 NotI
TTCTGCCTCCTCTGGGAATTCGGTACCGCGGCCGCCTAAGGCCTCACCCTGCGATCCGAATGCTTTATTGTGAAATTGTGA
TGCTATTGCTTTATTTGTAACATTATAGCTGCAATAAACAAATTGGTAATATTCGACGTTATTTGTTGTTAACAACAATTGCA
AATAAACACTTAAACATTACGATATACGAAATAAACATTGGTAATATTCGACGTTATTTGTTGTTAACAACAATTGCA
                                                     SpeI    rITR-F
TTCATTTTATGTTTCAGTTCAGGGGAGGTGTGGGAGGTTTTTTAAACTAGTCCACTCCCTCTCTGCGCTCTGCTCGCT
                                    SmaI   SmaI
CACTGAGGCCGGGCGACCAAAGGTCGCCCGACGCCCGGGCTTTGCCCGGGCCGGCCTCAGTGAGCGAGCGAGCGCGCAGAGA
  PstI
GGGACTGCAGAATACTCTCGACAATTCACTCGTTTACAACGTCGTGACTGGGAAAACCCTGGCGTTACCCAACT
```

FIG. 8 (continued)

P mU7-SA6Es-IND9

```
           BP       PPT              SA           ESE                                           Bpi
GCAACTGACCATGTTTCTTTTTTTCTGCAGACGAATCCTGCTGAACGACGAACAACCACCGGAGTCTTCTTATGA
                                                                   Bpi
AGACTCTTCG
```

Q

CMV-SA6GE12MS

```
       U2snRNA complementary    BP              PPT              SA          ESE
ATTCGGATAGAGGATGTATGATATTACTGACCATGTTTCTTTTTTTCTGCAGACGAATCCTGCTGAACAAGACGGAC
                                                        Sm                 Bpi
GAAGAAGCGGAGACAGCGACGAAGAACAACCAACACACACTGACCACAATTTTTGAACCGGAGAGTCTTC
         Bpi
TTATGAAGACTCTTCG
```

R

```
    BsaI         Hairpin CB20          IND9
TTTCGCAGGTCTCCACCGNNNNNNNNNNNNNNATTCGTCTGCGGTGGTTCTCGTCGTGCTGCTCGTTCG
TGAGACCGCAGGTT
BsaI
```

METHODS AND COMPOSITIONS FOR SINGLE CELL EXPRESSION PROFILING

CROSS-REFERENCE TO RELATED APPLICATIONS

Pursuant to 35 U.S.C. §119(e), this application claims priority to U.S. Provisional Application Ser. No. 61/752,233 filed on Jan. 14, 2013, the disclosure of which is herein incorporated by reference.

STATEMENT REGARDING FEDERALLY SPONSORED RESEARCH

This invention was made with government support under Grant No. HHSN261201300032C awarded by the National Cancer Institute. The government has certain rights in the invention.

INTRODUCTION

Advances in genomics research have been instrumental in accelerating the pace of biomarker and drug discovery. One promising approach for facilitating the process of disease diagnosis, as well as drug target identification and validation, is gene expression profiling. Transcriptional profiling of RNA and measurements of protein presence or abundance can be used for diagnosis, for example, where expression, overexpression, or lack of expression of a particular gene or set of genes (e.g., a panel of genes) correlates with a given disease state or predisposition. Similarly, where copy number (amplification, deletion or disruption) of a gene sequence at the chromosomal level correlates with a disease or disease predisposition, determination of DNA copy number and corresponding changes in gene expression level in an individual or in a tissue or cell type can predict or diagnose that disease.

Conventional transcription profiling methods are based on DNA microarray technology, for example, as reviewed in Greenberg (2001) *Neurology* 57:755-61; Wu (2001), *J. Pathol.* 195:53-65; Dhiman et al. (2001) *Vaccine* 20:22-30; Bier et al. (2001) Fresenius *J. Anal. Chem.* 371:151-6; Mills et al. (2001) *Nat. Cell Biol.* 3:E175-8; and as described in U.S. Pat. Nos. 5,593,839; 5,837,832; 5,856,101; 6,203,989; 6,271,957; and 6,287,778. The DNA microarray approach enables simultaneous comparison of the expression of several thousand genes in a given sample by assessing hybridization of the labeled polynucleotide samples, obtained by reverse transcription of mRNAs, to the DNA molecules attached to the surface of the test array.

SUMMARY

Methods of obtaining a single cell expression profile from a target mammalian cell are provided. Aspects of the methods include contacting a cellular sample which includes the target mammalian cell with a packaged viral barcoded trans-splicing library including a plurality of barcoded trans-splicing constructs under transduction conditions, where a barcoded trans-splicing construct includes a trans-splicing element linked to a barcode element. The methods further include generating expression data from the resultant transduced target mammalian cell to obtain the single cell expression data from the target mammalian cell. Also provided are compositions, e.g., libraries and components thereof, which find use in practicing the methods.

BRIEF DESCRIPTION OF THE FIGURES

FIG. 7, Panel B shows a comparison of data obtained using multiplex and single-plex qRT-PCR formats.

FIG. 8A-FIG. 8R provides nucleic acid sequences of constructs useful for practicing the subject methods according to certain aspects of the present disclosure.

DETAILED DESCRIPTION

Figure 1:
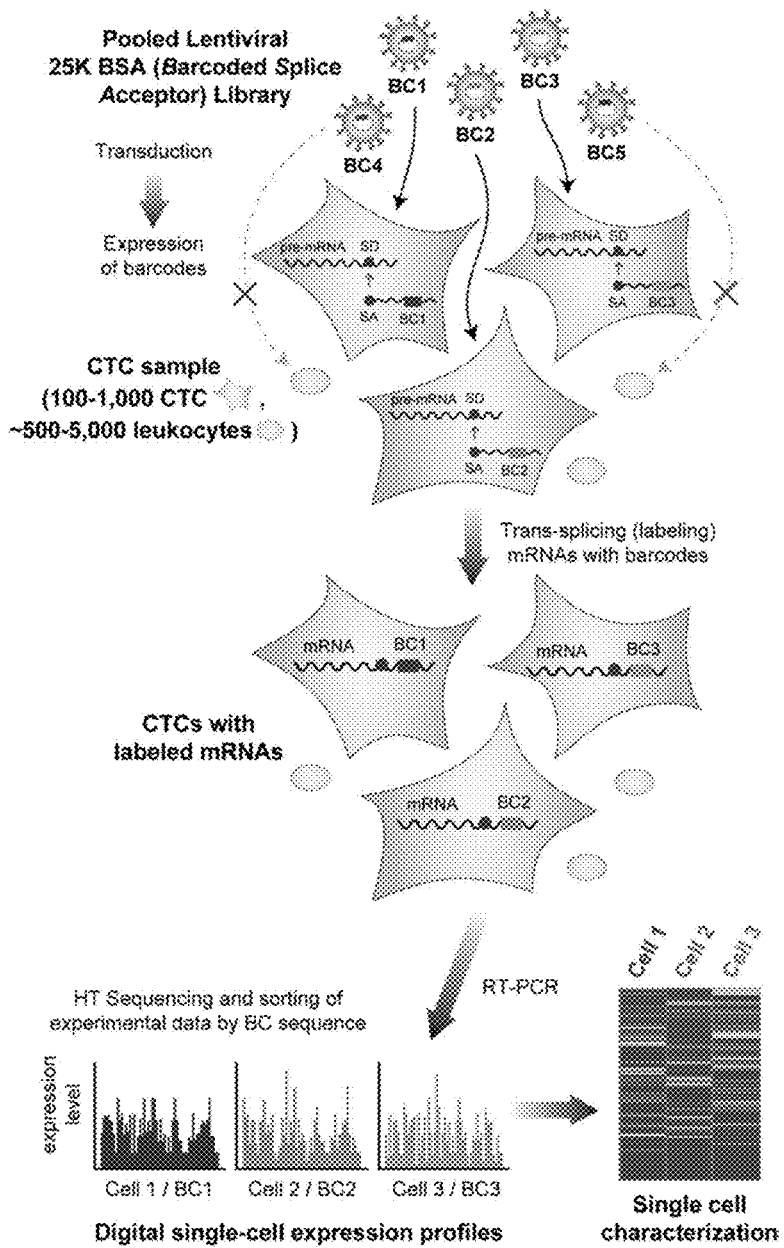
FIG. 1 schematically illustrates contacting a cellular sample with a packaged viral barcoded trans-splicing library and generating single-cell expression data from target transduced cells according one embodiment of the present disclosure.

Methods of obtaining a single cell expression profile from a target mammalian cell are provided. Aspects of the methods include contacting a cellular sample that includes the target mammalian cells, which may be a heterogeneous cell population, with a packaged viral barcoded trans-splicing library including a plurality of barcoded trans-splicing constructs under transduction conditions, where a barcoded trans-splicing construct includes a trans-splicing element linked to a barcode element. Aspects of embodiments of the methods further include labeling mRNAs in the resultant transduced cells with cell-specific barcodes expressed in the cells, followed by quantitation of the barcoded mRNAs to obtain the single cell expression data. Also provided are compositions, e.g., libraries and components thereof, which find use in practicing the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, methods of obtaining a single cell expression profile from a target mammalian cell are provided. By "single cell expression profile" is meant the expression level of a gene of interest in a cell (e.g., as determined by quantitating the level of an RNA or protein encoded by the gene of interest), or a set of expression levels of a plurality (e.g., 2 or more) of genes of interest. In certain aspects, the single cell expression profile includes target cell expression level data for 1, 2 or more, 5 or more, 10 or more, 20 or more, 50 or more, 100 or more, 200 or more, 300 or more, 400 or more, 500 or more, 1,000 or more, 5,000 or more, e.g., 10,000 or more genes of interest. According to one embodiment, the single cell expression profile includes target cell expression level data of from 50 to 1000 genes of interest, e.g., from 100 to 500 genes of interest. In certain aspects, the methods include detecting and/or quantitating the expression of all or substantially all of the genes transcribed in the target cell, such that a single cell expression profile on a genome-wide scale is obtained. For example, in certain aspects, the genes represented in the single cell gene expression profile include 50% or more, 60% or more, 70% or more, 80% or more, 90% or more, 95% or more, or 100% of the genes expressed (e.g., transcribed) in the target cell. The expression profile of the method of the invention may be performed for the individual, subset or complete set of alternatively spliced RNAs expressed from the gene or genomic element included in the assay, as desired. The terms "expression" and "gene expression" include transcription and/or translation of nucleic acid material. For example, gene expression profiling may include detecting and/or quantitating one or more of any RNA species transcribed from the genomic DNA of the target cell, including pre-mRNAs, mRNAs, non-coding RNAs, microRNAs, small RNAs, regulatory RNAs, and any combination thereof. Expression levels of an expressed sequence are optionally normalized by reference or comparison to the expression level(s) of one or more control expressed genes, including but not limited to, ACTB, GAPDH, HPRT-1, RPL25, RPS30, and combinations thereof. These "normalization genes" have expression levels that are relatively constant among target cells in the cellular sample.

According to certain embodiments, the expression profile includes "binary" or "qualitative" information regarding the expression of each gene of interest in a target cell. That is, in such embodiments, for each gene of interest, the expression profile only includes information that the gene is expressed or not expressed (e.g., above an established threshold level) in the target cell. In other embodiments, the expression profile includes quantitative information regarding the level of expression (e.g., based on rate of transcription, rate of splicing and/or RNA abundance) of one or more genes of interest. In certain aspects, the quantitative information regarding gene expression levels is obtained by measuring transcription and/or splicing (e.g., trans-splicing) of pre-mRNAs rather than the steady state levels of mature mRNAs, where the steady-state levels of mature mRNAs depends on additional processing, transport and turnover steps in the nucleus and cytoplasm. According to one embodiment, when gene expression levels are based on transcription and/or splicing (e.g., trans-splicing) of pre-mRNAs, the transcribed and/or spliced pre-mRNAs measured are those present in the target cell within 12 hours, within 11 hours, within 10 hours, within 9 hours, within 8 hours, within 7 hours, within 6 hours, within 5 hours, within 4 hours, within 3 hours, within 2 hours, or within 1 hour or less after transduction of the target cell. In other aspects, gene expression levels are based on the steady state levels of mature mRNAs in the transduced target cell. A qualitative and/or quantitative expression profile from the target cell may be compared to, e.g., a comparable expression profile generated from other target cells in the cellular sample and/or one or more reference profiles from cells known to have a particular biological phenotype or condition (e.g., a disease condition, such as a tumor cell; or treatment condition, such as a cell treated with an agent, e.g., a drug). When the profiles being compared are quantitative expression profiles, the comparison may include determining a fold-difference between one or more genes in the expression profile of a target cell and the corresponding genes in the expression profile(s) of one or more different target cells in the cellular sample, or the corresponding genes in a reference cell or cellular sample. Alternatively, or additionally, the single cell expression profile may include information regarding the relative expression levels of different genes in a single target cell. In certain aspects, the fold difference in intercellular expression levels or intracellular expression levels can be determined to be 0.1 or more, 0.5 fold or more, 1 fold or more, 1.5 fold or more, 2 fold or more, 2.5 fold or more, 3 fold or more, 4 fold or more, 5 fold or more, 6 fold or more, 7 fold or more, 8 fold or more, 9 fold or more, or more than 10 fold or more, for example.

The expression profile may be indicative of the biological condition of the cell including but not limited to a disease condition (e.g., a cancerous condition, metastatic potential, an epithelial mesenchymal transition (EMT) characteristic, and/or any other disease condition of interest), the condition of the cell in response to treatment with any physical action (e.g., heat shock, hypoxia, normoxia, hydrodynamic stress, radiation, and/or the like), the condition of the cell in response to treatment with chemical compounds (e.g., drugs, cytotoxic agents, nutrients, salts, and/or the like) or biological extracts or entities (e.g., viruses, bacteria, other cell types, growth factors, biologics, and/or the like), and/or any other biological condition of interest (e.g. immune response, senescence, inflammation, motility, and/or the like). The expression profile may be used to reveal heterogeneity in the target cell population and classify (or sub-classify) a target cell within a cellular sample (e.g., a clinical sample).

The target mammalian cell may be any mammalian cell of interest to a practitioner of the subject methods. By "target mammalian cell" is meant a mammalian cell present in a cellular sample obtained from a mammal. As described in further detail below, the cellular sample may be made up of a collection or mixture of heterogeneous cells with different phenotypes. In some instances, the population of cells with the same phenotype can be also heterogeneous at the gene expression level. The mammal may be human, rat, mouse, rabbit, monkey, baboon, chicken, bovine, porcine, ovine, canine, feline, or any other mammal of interest. In certain aspects, the cellular sample is derived from a biological fluid sample (e.g., blood, saliva, a bone marrow suspension, cerebrospinal fluid, gastric fluid, synovial fluid, urine, lymph, semen, seminal fluid, mucus, tears, sweat, amniotic fluid or the like), a tissue sample (e.g., a tissue sample from brain, lung, breast, skin, heart, colon, pancreas, prostate, ovary, testis, cardiac muscle, skeletal muscle, adipose tissue, or the like) or a cell culture. In some embodiments, the target cell (e.g., a human target cell) is grown in a model organism (e.g., xenograft model of cancer in mice) prior to expression analysis. The target mammalian cell may be a disease-free cell or a diseased cell. By "diseased" is meant any condition or disorder that damages or interferes with the normal function of a cell, tissue, or organ. In certain aspects, when the target mammalian cell is a diseased cell, the cell is a tumor cell. As used herein, a "tumor cell" or "cancer cell" is a cell which exhibits abnormal changes in proliferation, cell death, cell metabolism, cell signaling, immune response, replicative control, and/or motility due to environmental, genetic or epigenetic factors. The tumor cell may be derived from cancers of the colon, breast, lung, prostate, skin, pancreas, brain, kidney, endometrium, cervix, ovary, thyroid, or other glandular tissue carcinomas or melanoma, lymphoma, or any other cancers of interest. In certain aspects, the target cell is a tumor cell derived from genetically modified cells or cells treated with mutagenic and/or cancer-causing agents.

Packaged viral barcoded trans-splicing libraries employed in the subject methods are made of a plurality of barcoded trans-splicing constructs, where each barcoded trans-splicing construct includes a trans-splicing element linked to a barcode element. As used herein, a "trans-splicing element" is an element that includes nucleotide sequences (e.g., one or more splice acceptor and/or splice donor sequences, one or more binding sequences, one or more regulatory motifs, a spliced leader sequence, and/or the like) necessary for an RNA transcribed from the barcoded trans-splicing construct in the transduced target mammalian cell to participate in a trans-splicing reaction with an endogenous pre-mRNA in the target mammalian cell.

While not being bound by any particular theory, the biochemical mechanism may be characterized as follows. Introns are removed from primary transcripts by cleavage at conserved sequences called splice sites. These sites are found at the 5' and 3' ends of introns. Most commonly, the intronic RNA sequence that is removed begins with the dinucleotide GU at its 5' end, and ends with AG at its 3' end. The consensus sequences surrounding splice sites (e.g., a splice donor site at the 5' end of intron and a splice acceptor site at the 3' end of the intron) are known to be critical, because changing one of the conserved nucleotides results in inhibition of splicing. Upstream (5'-ward) from the AG in the splice acceptor site is a region high in pyrimidines (C and U) referred to as the polypyrimidine tract (PPT). Another important sequence occurs at what is called the branch point, located anywhere from 18 to 40 nucleotides upstream from the 3' end of an intron. The branch point always contains an adenine, but it is otherwise loosely conserved. A typical sequence is YNYYRAY, where Y indicates a pyrimidine, N denotes any nucleotide, R denotes any purine, and A denotes adenine. The splice donor site is more compact than the splice acceptor site and has the consensus sequence AG^GURAGU. In addition to consensus sequences at their splice sites, eukaryotic genes also contain exonic splicing enhancers (ESEs) and intronic splicing enhancers (ISEs). These sequences, which may help position the splicing apparatus, are mainly found in the exons of genes and bind proteins that recruit splicing machinery to the correct site. The splicing process occurs in organelles called spliceosomes. Pre-mRNAs (or hnRNA) contain sequence elements including a 5' splice donor site, branch point, a polypyrimidine tract and a 3' splice acceptor site recognized and utilized during spliceosome assembly.

In certain aspects, the trans-splicing element is a spliceosome-recognized trans-splicing element. The spliceosome-recognized trans-splicing element may include a splice acceptor, a splice donor, or a splice acceptor and a splice donor. In spliceosome-recognized trans-splicing elements that include a splice acceptor, the splice acceptor may include a branchpoint, a polypyrimidine tract, and a 3' splice site. The trans-splicing element may include any other sequences to facilitate trans-splicing or enhance the efficiency thereof, e.g., an exonic splicing enhancer ("ESE"). According to certain embodiments, the spliceosome-recognized trans-splicing element that includes a branchpoint, polypyrimidine tract, and a 3' splice acceptor site further includes a 5' splice donor site. Trans-splicing, including considerations and nucleotide sequences useful for the design of trans-splicing elements, are described, e.g., in Garcia-Blanco (2003) *J. Clin. Invest.* 112:474-480; Mansfield et al. (2004) *Trends in Mol. Med.* 10(6):263-268; Viles and Sullenger (2008) *RNA* 14:1081-1094; Wood et al. (2007) *PLoS Genetics* 3(6):e109; Yang and Walsh (2005) *Molecular Therapy* 12(6):1006-1012; Gruber et al. (2011) *Mol. Cancer Ther.* 10:233-241; Singh and Cooper (2012) *Cell* 18:472-482; Wally et al. (2012) *J. Investig. Dermatol.* 132:1959-1966; Yang and Walsh (2005) *Mol. Therapy* 12:1006-1012; and Hammond and Wood (2011) *Trends Genet.* 27(5):196-205. According to certain embodiments, the labeling of RNAs (e.g., mRNAs) with specific barcodes is catalyzed by additional RNA processing or modification mechanisms, which can be spliceosome-dependent or independent, including trans-splicing ribozymes (see, e.g., Fiska and Birgisdottir (2010) *New Biotechnol.* 27:194-203), exon shuffling (see, e.g., Al-Balool et al. (2011) *Genome Research* 21:1788-1799), template-switching, sequence-specific oligonucleotide trans-splicing, CRISPR-mediated recombination, and/or the like.

The splice site in the trans-splicing element may be a promiscuous or sequence specific splice site. By "promiscuous splice site" is meant the splice site is designed to permit non-specific trans-splicing to the target pre-mRNA sequence. Inclusion of a promiscuous splice site in the trans-splicing element may increase the trans-splicing efficiency and uniform labeling of different mRNAs in the transduced target cell. Increasing the promiscuity of the splice site may be achieved, e.g., by modifying the three-dimensional structure and/or sequence of branch point and/or pyrimidine tract sequences, or by including one or more additional splice sites and/or regulatory elements such that they are more efficient splicing elements. In certain aspects, a splice leader sequence (e.g., which mimics or is complementary to at least a portion of the spliceosome snRNA, such as a U1, U2, U4, U5, U7 and/or U6 snRNA), is included in a splice donor or splice acceptor trans-splicing element to increase promiscuous trans-splicing activity. According to one embodiment, a splice acceptor site sequence and/or a splice donor site sequence is included in the structure of a snRNA, such as a modified U7 snRNA, U5 snRNA and/or the like. According to certain embodiments, the trans-splicing element includes an RNA polymerase pause or termination site in a splice donor- and/or splice-acceptor-containing trans-splicing element to increase the efficiency of the trans-splicing reaction. Alternatively, or additionally, promiscuity of the trans-splicing element is increased by excluding sequences in the trans-splicing element which could interact with specific pre-mRNA sequences. In certain aspects, a pre-mRNA target binding domain is included in the trans-splicing element to facilitate labeling a specific sub-population of mRNAs, e.g., a fraction of RNAs having a specific conserved nucleotide sequence. Such trans-splicing elements with mRNA binding domains have been used to correct genetic defects in mRNA splicing and delivery of suicidal trans-spliced constructs to cancer cells.

As described above, the trans-splicing element may include a splice donor. The use of splice donors in trans-splicing is described, e.g., in Lasda and Blumenthal (2011) Trans-splicing (Wiley Interdiscip. Rev.) *RNA* 2:417-433; Blumenthal (1993) *Bioassays* 15:347-348; Bruzik and Maniatis (1992) *Nature* 360:692-695; Jaladat et al. (2011) *RNA Biology* 8:372-377; and Horiuchi and Aigaki (2006) *Biol. Cell* 98:135-140. Trans-splicing elements which include a splice donor may include a regulatory sequence such as a spliced leader sequence, splice enhancer, snRNA-interaction domain, and other sequences which facilitates/promotes trans-splicing in mammalian cells.

The plurality of barcoded trans-splicing constructs employed in the subject methods may include constructs that each include a trans-splicing element linked to a barcode element. By "linked" is meant the trans-splicing element and barcode element are present in the same nucleic acid molecule, and that upon transcription of the construct in a transduced target cell, the barcode element is present in any fusion transcripts generated via trans-splicing in the transduced target cell. As used herein, a "barcode element" is a barcode nucleic acid sequence. The phrases "barcode nucleic acid sequence" and "barcode", as well as variations thereof, refer to an identifiable nucleotide sequence, such as an oligonucleotide or polynucleotide sequence. In some embodiments, nucleic acid barcodes are uniquely identifiable. In some embodiments, a nucleic acid barcode can comprise a synthetic or natural nucleic acid sequence, DNA, RNA, or other nucleic acids and/or derivatives. For example, a nucleic acid barcode can include nucleotide bases adenine, guanine, cytosine, thymine, uracil, inosine, or analogs thereof. The barcode length may vary as desired, where in some instances the length ranges from 2 to 100 nt, such as 5 to 25 nt, and in some embodiments including from 8 to 22 nt. A given barcode sequence may vary as desired. As desired, barcodes may be any sequence of 2-10 (or more) random nucleotides (e.g. A, G, C or T in every position or subset of these nucleotides). In some instances, barcodes employed are specially designed with specific unique (i.e., distinct) sequences that are significantly different from each other, even in the case of at least 1 or even 2 mutations. Barcode sequences may be present in the splice element in linear form or secondary structure form, e.g., a stem-loop RNA structure or the like in order to increase promiscuity of the trans-splicing reaction. In certain aspects, a trans-splicing element may serve as both a trans-splicing element and a barcode. For example, a trans-splicing element may be modified by introducing point mutations which result in the element having a barcode, and which mutations do not affect the functionality of the trans-splicing element. The developed plurality/library of functional trans-spliced elements could be used as both trans-splicing element and barcode.

According to certain embodiments, the plurality of barcoded trans-splicing constructs included in the packaged viral barcoded trans-splicing library each has a distinct barcode element linked to a common trans-splicing element. As described in more detail below, the distinct barcode may serve to uniquely identify transcripts from the transduced target mammalian cell among other transduced cells (e.g., additional target mammalian cells) in the cellular sample, by virtue of the target mammalian cell having transcripts labeled with the distinct barcode as a result of trans-splicing between endogenous pre-mRNAs of the target mammalian cell and RNA transcripts expressed from the barcoded trans-splicing construct present in the cell.

In certain aspects, the trans-splicing construct includes two different trans-splice elements, each linked to a different barcode. The two different barcoded trans-splicing elements may be expressed from the same promoter or different promoters. According to one embodiment, one such element is a barcoded splice acceptor and another such element is a barcoded splice donor site, where the elements are expressed from two different promoters in the same construct. The presence of barcoded splice donor and splice acceptor transcripts allow them to label each other and other barcoded splicing element transcripts which may be present in the transduced cell.

Within a given packaged viral barcoded trans-splicing library, the number of distinct barcode elements (e.g., distinct barcode elements linked to a common trans-splicing element) may vary. In certain aspects, the complexity of the library (e.g., the number of distinct barcode elements) is greater than the number of cells for which the library is designed to transduce. For example, the complexity of the library may be 2-fold or more, 3-fold or more, 4-fold or more, 5-fold or more, 6-fold or more, 7-fold or more, 8-fold or more, 9-fold or more, e.g., 10-fold or more greater than the number of cells for which the library is designed to transduce. According to certain embodiments, the barcoded trans-splicing library includes 10 or more, 50 or more, 100 or more, 500 or more, 1000 or more, 10,000 or more, 100,000 or more, 500,000 or more, or 1,000,000 or more barcoded trans-splicing constructs each having a distinct barcode element. In certain aspects, the number of distinct barcodes in the trans-splicing library is about 100,000.

The barcoded trans-splicing constructs may include one or more promoter sequences. A "promoter sequence" (also referred to herein as a promoter) is a DNA regulatory region capable of binding RNA polymerase in a cell and initiating transcription of a sequence (e.g., a coding sequence) to which the promoter is operably linked. For example, the promoter sequence may be bounded at its 3' terminus by the transcription initiation site and extend upstream (in the 5' direction) to include the minimum number of bases or elements necessary to initiate transcription at levels detectable above background. Within the promoter sequence may be found a transcription initiation site, as well as protein binding domains responsible for the binding of RNA polymerase or other transcriptional factors. Eukaryotic promoters will often, but not always, contain BRF, TATA, Inr and DPE elements in the core promoter and different enhancer and regulatory elements upstream or downstream of core promoter. Various promoters, such as those recognized by RNA polymerase II or RNA polymerase III and/or inducible promoters known in the art may be used to drive the various vectors of the present invention. In certain aspects, the promiscuity of trans-splicing is increased by incorporating a 5' CAP structure into the barcoded trans-splicing construct and expressing the construct from a promoter recognized by RNA polymerase II. If both splice acceptor and splice donor elements are present in the transplicing construct, both splice elements could be expressed in the cells from a single promoter or from two different promoters. In the case of expression of splice elements from two promoters, the splice acceptor element and splice donor element may be present in the different transcripts and may trans-splice to each other in the transduced cells.

The promoter/enhancer(s) for transcribing the barcoded trans-splicing construct in the target mammalian cell, expression of effector sequences present in the construct (e.g., as described in greater detail below), as well as any drug-resistance or reporter cassettes included in the construct, may be selected based on the desired expression pattern (e.g., cell type-specific expression) of the barcoded trans-splicing construct, effector sequence, drug-resistance and/or reporter cassettes, and the specific properties of the promoters/enhancers. Thus, the promoter may be a constitutive promoter, such as the ubiquitin C, CMV, β-actin, U5 snRNA, U7 snRNA, EF-1alfa or PGK promoters controlled by RNA polymerase II, or the U6 snRNA, H1 histone, or tRNA promoters controlled by RNA polymerase III. Alternatively, the promoter may be a tissue-specific promoter such as lck, myogenin, or thy1 promoters. In addition, promoters may be selected to allow for inducible expression of one or more elements in the construct, e.g., the barcoded trans-splicing RNA and/or an effector element. A number of systems for the inducible expression using such a promoter are known in the art, including the tetracycline responsive system, the lac operator-repressor system, and cre-lox recombination-induced transcription system. An enhancer also may be present to increase expression of one or more elements present in the construct. For example, a CMV enhancer may be used in combination with the chicken β-actin promoter.

In those embodiments employing viral vectors in the barcoded trans-splicing construct libraries, members of the barcoded trans-splicing construct library are present as viral particles that house a viral genomic nucleic acid, where the viral genomic nucleic acid of a given particle member of the library includes both a vector domain and a barcoded trans-splicing construct (i.e., barcoded trans-splicing libraries where the barcoded trans-splicing construct-encoding nucleic acid is encapsidated in a viral protein shell). Such libraries may be referred to as packaged viral barcoded trans-splicing libraries. Of particular interest in certain embodiments is the use of packaged viral barcoded trans-splicing libraries that employ viral vector domains that provide for entry of a single barcoded trans-splicing construct into a given target cell (e.g., the target mammalian cell) in the cellular sample.

Within a packaged viral barcoded trans-splicing library of the invention, the viral genomic nucleic acids of different library members will share common vector domains. Accordingly, the barcoded trans-splicing construct members will share a common vector sequence, such that the sequence of the encapsidated viral genomic nucleic acids in the library will be substantially, if not completely, identical, but for the barcoded trans-splicing constructs of the library. The sequence of the vector domain may vary greatly, depending on the nature of the vector. In some instances, the vector domain includes sequences necessary for the production of recombinant viral constructs in a packaging cell, transduction and replication of barcoded trans-splicing construct in the target cells and expression of the barcoded trans-splicing construct, reporters or other effectors and genes. Generation of the vector domain, as well as barcoded trans-splicing construct libraries including the same, can be accomplished using any suitable genetic engineering techniques, including without limitation, the standard techniques of PCR, oligonucleotide synthesis, restriction endonuclease digestion, site-specific digestion, site-specific recombination, ligation, transformation, plasmid purification, and DNA sequencing.

In some instances, the vector domain is selected from a viral genome of a virus selected from the group of adenoviral, adeno-associated, vaccinia, herpes, foamy, etc. viruses, where such viruses are commonly used for gene transfer applications. In some instances, the vector domain is a retroviral vector region, such that it is a domain derived from a retrovirus. Retroviruses are any virus belonging to the family Retroviridae, comprising single-stranded RNA animal viruses characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus may then be capable of integrating into the host genome (e.g., the genome of the target mammalian cell). Accordingly, in certain aspects, the barcoded trans-splicing construct is configured to integrate into the genome of the target mammalian cell. The integration may be non-specific or specific to a particular chromosomal location. In certain aspects, the viral vector is designed to integrate at a specific chromosomal site using site-specific recombination (e.g., using a Cre-Lox or other recombination system), zinc finger endonuclease, CRISPR endonuclease, at a specific site at which the virus from which the vector is derived naturally integrates, or the like. Viral barcoded trans-splicing constructs with site-specific integration can be employed for long-term expression profiling, e.g., during the course of tumor growth.

In certain aspects, the barcoded trans-splicing vector is a non-integrating vector, e.g., where the barcoded trans-splicing construct is based on a non-integrating lentiviral, adenoviral or adeno-associated viral vector. According to certain embodiments, a non-integrating trans-splicing construct is used to measure gene expression within 1 hour, within 2 hours, within 3 hours, within 4 hours, within 5 hours, within 6 hours, within 7 hours, within 8 hours, within 9 hours, within 10 hours, within 11 hours, or within 12 hours of transduction of the target cell. The non-integrated barcoded TS constructs may be stable in the cells for several divisions and, in certain aspects, can be used for expression profiling up to 1-2 weeks after transduction step.

According to certain embodiments, the retroviral vector region is an adeno-associated viral vector region, e.g., a vector derived from an adeno-associated virus (AAV). Any suitable AAV-based vector with any serotype of interest may be used, including AAV-based vectors described, e.g., in McCarty (2008) *Mol. Therapy* 16:1648-1656; Nonnenmacher (2012) *Gene Therapy* 19:649-658; and Jayandharan et al. (2008) *Gene Therapy* 15:1287-1293.

In some instances, the retroviral vector region is a lentiviral vector region, e.g., a vector derived from a lentivirus. Lentiviruses are members of the retrovirus family. Lentivirus vectors may be pseudotyped with VSV-G, and have been derived from the human immunodeficiency virus (HIV), the etiologic agent of the human acquired immunodeficiency syndrome (AIDS); visan-maedi, which causes encephalitis (visna) or pneumonia in sheep; the caprine arthritis-encephalitis virus, which causes immune deficiency, arthritis, and encephalopathy in goats; equine infectious anemia virus (EIAV), which causes autoimmune hemolytic anemia and encephalopathy in horses; feline immunodeficiency virus (FIV), which causes immune deficiency in cats; bovine immune deficiency virus (BIV) which causes lymphadenopathy and lymphocytosis in cattle; and simian immunodeficiency virus (SIV), which causes immune deficiency and encephalopathy in non-human primates. Vectors that are based on HIV may retain <5% of the parental genome, and <25% of the genome may be incorporated into packaging constructs, which minimizes the possibility of the generation of revertant replication-competent HIV. The vector region may include sequences form the 5' and 3' LTRs of a lentivirus. In some instances, the vector domain includes the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Where desired, the packaged viral barcoded trans-splicing library may be made up of self-inactivating vectors that contain deletions of the regulatory elements in the downstream long-terminal-repeat sequence, eliminating transcription of the packaging signal that is required for vector mobilization. As such, the vector region may include an inactivated or self-inactivating 3' LTR. The 3' LTR may be made self-inactivating by any convenient method. For example, the U3 element of the 3' LTR may contain a deletion of its enhancer sequence, such as the TATA box, Sp1 and NF-kappa B sites. As a result of the self-inactivating 3' LTR, the provirus that is integrated into the host cell genome will comprise an inactivated 5' LTR. Optionally, the U3 sequence from the lentiviral 5' LTR may be replaced with a promoter sequence in the viral construct. This may increase the titer of virus recovered from the packaging cell line. An enhancer sequence may also be included. In certain aspects, the barcoded trans-splicing viral construct is a non-integrating lentiviral construct, where the construct does not integrate by virtue of having a defective (e.g., by site-specific mutation) or absent integrase gene. Integrase-defective lentiviral vectors are described, e.g., in Banasik and McCray (2010) *Gene Therapy* 17(2):150-157.

The viral genomic nucleic acids of the barcoded trans-splicing libraries also may contain additional elements, where such elements may vary greatly. For example, a reporter gene may be placed in functional relationship with the internal promoter, such as the gene for a fluorescent marker protein. If a marker gene is expressed from a promoter along with the trans-spliced element, an additional splice donor site, or combination of splice donor and splice acceptor site can be included. Alternatively, the additional genetic elements can be operably linked with and controlled by an independent promoter/enhancer.

In another embodiment, the trans-spliced viral construct may include an effector cassette, e.g., as described in more detail below and in co-pending U.S. Provisional Patent Application No. 61/644,324 filed on May 8, 2012, the disclosure of which is herein incorporated by reference. The term "effector" is used to refer to a biochemical molecule that can effect the transcription, translation, expression, processing or function of another molecule or molecules, such as a target gene or the product of a target gene. Effectors may be full-length proteins, protein domains, peptides, single-stranded or double-stranded deoxy- or ribo-oligonucleotides, siRNAs, micro RNAs, CRISPR RNAs, ribozymes, antisense RNAs, regulatory RNAs including small RNAs and non-coding RNAs, or mimetics or analogues thereof. Effector cassettes of interest include at least an effector sequence, where the effector sequence may be operationally-linked to a promoter, e.g., for expression of the effector sequence in a cell that includes the effector construct. Optionally, an effector cassette may include an effector-specific barcode, e.g., to facilitate identification of effector sequence.

The libraries employed in embodiments of the subject methods can be produced using any convenient protocol. For example, the viral and barcoded trans-splicing domains can be generated synthetically or enzymatically by a number of different protocols, and the appropriate oligonucleotide and polynucleotide constructs may be purified using standard recombinant DNA techniques as described in, for example, Sambrook et al., Molecular Cloning: A Laboratory Manual, 3rd Ed., Cold Spring Harbor Press, Cold Spring Harbor, N.Y. (2000), and under regulations described in, e.g., United States Dept. of HHS, National Institute of Health (NIH) Guidelines for Recombinant DNA Research. Where desired, the barcoded trans-splicing constructs may be synthesized synthetically using phosphoramidite chemistry. In some instances, the barcoded trans-splicing constructs are synthesized using an array-based protocol (e.g., on a surface using photolithography, ink-jet deposition, electrochemical means, or the like). See e.g., U.S. Pat. No. 7,588,889 for a description of an example of such a protocol.

According to certain embodiments, preparing the barcoded trans-splicing libraries includes combining a barcoded trans-splicing construct (e.g., a pro-barcoded trans-splicing library including a trans-splicing element linked to a barcode element in an expression cassette) with a vector construct comprising a vector domain of vector sequence under conditions sufficient to produce transfection plasmids which, upon transfection of a packaging cell, result in the production of viral particles containing the barcoded trans-splicing construct as part of genomic nucleic acids encapsidated in viral protein shells. To prepare the product transfection plasmids used for transfection, a barcoded trans-splicing construct may be inserted into a vector nucleic acid, where any suitable protocol may be employed. Examples of suitable protocols include, but are not limited to: DNA ligase mediated joining, recombination enzyme mediate joining, using In-Fusion® PCR protocols (Clontech Laboratories, Mountain View, Calif.), Gateway® cloning technology (Life Technologies, Carlsbad, Calif.), and the like.

The resultant product transfection plasmids may then be used to transfect a suitable packaging cell line for production of barcoded trans-splicing library viral particles. The packaging cell line provides the viral proteins that are required in trans for the packaging of the viral genomic RNA into viral particles. The packaging cell line may be any cell line that is capable of expressing retroviral proteins, including HEK293, HeLa, D17, MDCK, BHK, NIH3T3, CHO, CrFK, and Cf2Th. In some embodiments, the barcoded trans-splicing construct is used together with a viral reporter construct which may comprise one or more reporter genes under the control of a constitutive or conditional (regulatable) promoter. The packaging cell line may stably express necessary viral proteins. Such a packaging cell line is described, for example, in U.S. Pat. No. 6,218,181. Alternatively, a packaging cell line may be transiently transfected with plasmids comprising nucleic acids that encode the necessary viral proteins. In another embodiment, a packaging cell line that does not stably express the necessary viral proteins is co-transfected with two or more plasmids. One of the plasmids comprises the viral construct comprising the trans-splicing construct. The other plasmid(s) comprises nucleic acids encoding the proteins necessary to allow the cells to produce functional virus that is able to infect the desired host cell. The packaging cell line may not express envelope gene products. In this case, the packaging cell line will package the viral genome into particles that lack an envelope protein. As the envelope protein is responsible, in part, for the host range of the viral particles, the viruses preferably are pseudotyped. A "pseudotyped" retrovirus is a retroviral particle having an envelope protein that is from a virus other than the virus from which the RNA genome is derived. The envelope protein may be from a different retrovirus or a non-retrovirus. One envelope protein is the vesicular stomatitis virus G (VSV-G) protein. Thus, the packaging cell line may be transfected with a plasmid that includes sequences encoding a membrane-associated protein, such as VSV-G, that will permit entry of the virus into a target cell. According to certain embodiments, the variety of capsid proteins from different serotypes, e.g. 1, 2, 3, 4, 5, 6 or DJ is used to pseudotype the trans-splicing libraries based on of adeno-associated viral vectors. One of skill in the art can choose an appropriate pseudo type specific and/or more efficient for the target cell used. In addition to conferring a specific host range, a chosen pseudotype may permit the virus to be concentrated to a very high titer. Viruses alternatively can be pseudotyped with ecotropic envelope proteins that limit infection to a specific species.

As summarized above, the cellular sample is contacted with a packaged viral barcoded trans-splicing library under transduction conditions. Transduction of one or more target cells in the cellular sample with the packaged viral barcoded trans-splicing library may be accomplished by any convenient protocol and may depend, at least in part, on the target cell type and the viral vectors employed. For example, transduction may include thawing a frozen packaged viral barcoded trans-splicing library, suspending the cellular sample in a cell culture medium (e.g., D-MEM) which may be supplemented with serum (e.g., 10% FBS) and/or a transduction enhancing agent (e.g., hexadimethrine bromide (Polybrene®)), combining the library and cell suspension in a cell culture plate, and placing the plate at 37° C. in a $CO_2$ incubator for a suitable period of time. In certain aspects, the cells are incubated for between 1 and 24 hours, such as between 4 and 16 hours, e.g., between 8 and 12 hours.

The transduction conditions may be optimized in order to achieve delivery and expression of a single unique barcoded trans-splicing construct into a given target cell. For example, in certain aspects, transducing any given target cell with a single unique barcoded trans-splicing construct is achieved by employing a sufficiently complex packaged viral barcoded trans-splicing library and carrying out the transduction step at a suitable multiplicity of infection (MOI), which is the ratio of infectious agents (e.g., viral particles) to target cells. According to certain embodiments, the transduction is carried out at an MOI of 1 or less, 0.9 or less, 0.8 or less, 0.7 or less, 0.6 or less, 0.5 or less, 0.4 or less, 0.3 or less, 0.2 or less, or 0.1 or less. Aspects of the invention include carrying out the transduction at an MOI of from 0.1 to 0.4, e.g., from 0.2 to 0.3.

In other aspects, the target cells are transduced at a high MOI (e.g., an MOI of 0.5 or more, 1 or more, 2 or more or 5 or more). High MOI transduction conditions find use, e.g., for profiling cellular samples in which it is difficult to control transduction efficiency of target cells (e.g. certain cancer biopsy samples, certain circulating tumor cells, etc.). In the case of transduction at high MOI (e.g., an MOI of 0.5 or greater), each transduced cell could express several trans-splicing constructs having distinct barcodes. Upon trans-splicing in the transduced cells, the single cell cellular mRNAs will be labeled with several unique barcodes, resulting in a redundant set of expression profiles for each transduced target cell.

Figure 4:
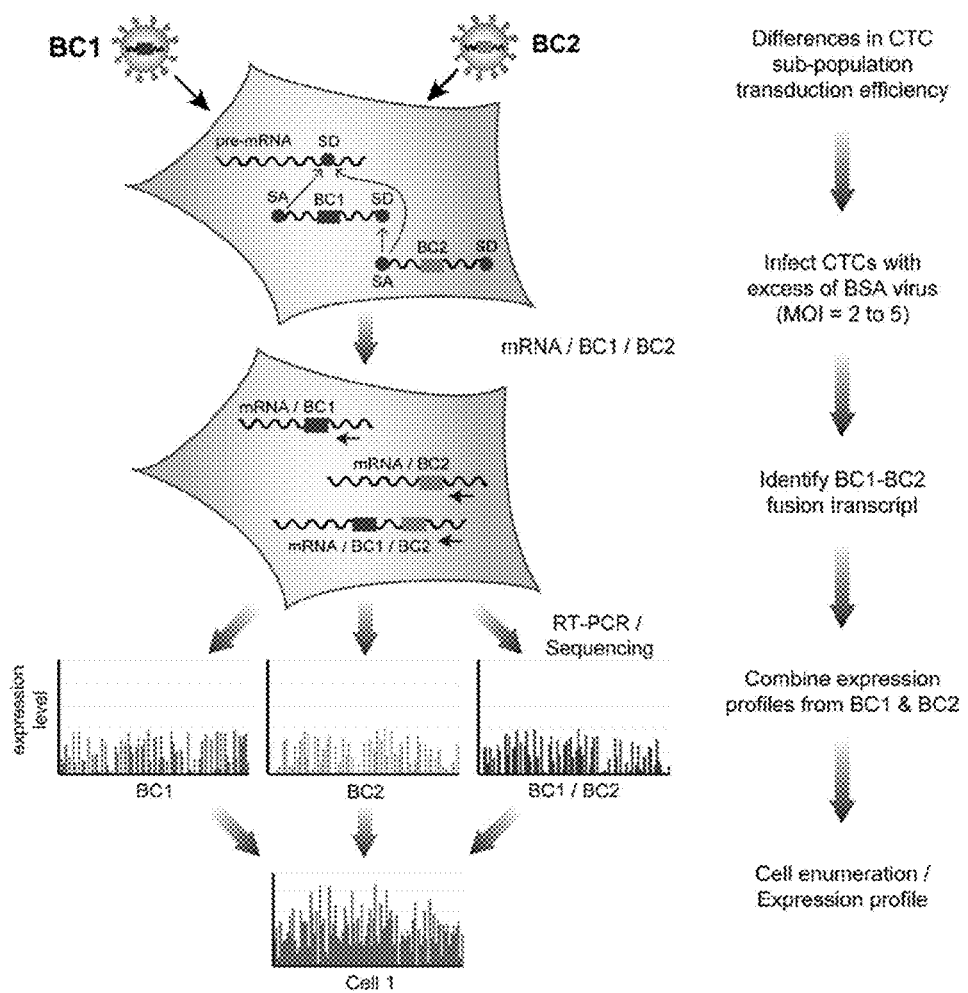
FIG. 4 schematically illustrates contacting a cellular sample with a packaged viral barcoded trans-splicing library and generating single-cell expression data from a target cell transduced with two different types of trans-splicing constructs having distinct barcodes according one embodiment of the present disclosure.

According to certain embodiments, trans-splicing constructs that include an additional splice-donor site (e.g., see FIG. 4) are trans-spliced to one another to generate in vivo double barcoded trans-spliced RNAs in the transduced target cell. These double-barcoded trans-spliced RNAs may be employed to identify the set of unique barcoded trans-splicing constructs present in the each transduced single cell.

The target cells can be a pure, homogeneous population of the same or similar phenotype cells, or the target cells can be a heterogeneous population of different cell types. In certain aspects, the target cells are the same or similar phenotypically, but are heterogeneous at the molecular level (e.g., may have significantly different gene expression profiles) due to the stochastic nature of transcription and RNA processing in mammalian cells. The target cells may be cultured, or may be present in tissues, organs, biological fluids or whole organisms, where the organism is (in some instances) a human, mouse or rat. The barcoded trans-splicing library may be co-transduced with a reporter plasmid in order to extend selection of target cells to a variety of in vivo and in vitro biological assays. Alternatively, the barcoded trans-splicing construct may itself include a reporter cassette for monitoring and/or selection of transduced cells.

As described above, the cellular sample may be a homogenous sample that includes a single type of cell, in which all cells of the cellular sample are targets for viral transduction and expression of the barcoded trans-splicing construct. In other aspects, the cellular sample is a heterogeneous cellular sample that includes different cell types. According to certain embodiments, the cellular sample is a heterogeneous sample, where it is desirable to express the barcoded trans-splicing construct in only a single type of target cell or a subset of target cell types in the cellular sample. One approach for selective expression of the barcoded trans-splicing construct in a target cell of interest is to operably link the trans-splicing and barcode elements to a promoter that is active in the desired type(s) of target cell(s) but is not active in the non-target cells (e.g., a cell-, tissue- and/or species-specific promoter).

A second approach for selective expression of the barcoded trans-splicing construct is to selectively transduce a particular type of target cell or subset of target cell types in a cellular sample by packaging the barcoded trans-splicing construct in a viral particle that is incapable of transducing (or does not efficiently transduce) non-target cells in the sample. For example, when the cellular sample is a heterogeneous sample that includes circulating tumor cells (CTCs) and leukocytes (e.g., a cellular sample derived from the blood of a cancer patient), the library may be packaged into viral particles that do not effectively transduce leukocytes. For example, the present inventors have discovered that leukocytes are naturally recalcitrant to infection with a lentiviral barcoded trans-splicing library.

Other approaches for selectively transducing a particular type of target cell or subset of target cells in the cellular sample is by modifying the tropism of the virus (that is, the specificity of a given virus for a cell type, tissue or species) such that the library only transduces the desired type(s) of cells in the cellular sample. There are two major types of viral tropism: the receptor-dependent and -independent tropisms. Restriction of viral replication occurs on the cell surface (receptor-dependent viral entry step) and/or intracellularly (receptor-independent post-entry replication steps). Any suitable approach for modifying the receptor-dependent and/or receptor-independent tropism of the packaged barcoded trans-splicing library may be employed. Modifying the tropism of viral vectors can be achieved by genetic modification of the viral envelope or capsid proteins, use of proteins derived from other enveloped viruses, use of targeting molecules derived from non-retroviral proteins expressed in the packaging cell line, use of adaptor or antibody molecules that retarget the virus to specific target cell-surface molecules, and/or any other approach suitable approach for modifying the tropism of the viral particles. For example, approaches for modifying viral tropism are described in McFadden et al. (2009) *Nature Reviews Immunology* 9:645-655; Turunen et al. (2002) *Mol. Ther.* 6:306-12; Kasahara et al. (1994) *Science* 266:1373-6; Cosset et al. (1995) *J Virol.* 69:6314-22; Valsesia-Wittmann et al. (1997) *EMBO J.* 16:1214-23; Battini et al. (1992) *J Virol.* 66:1468-75; Schnierle et al. (1997) *Proc Natl Acad Sci* 94:8640-5; Hatziioannou et al. (1999) *Hum Gene Ther.* 10:1533-44; Morizono et al. (2001) *J Virol.* 75:8016-20; Sandrin et al. (2002) *Blood* 100:823-32; Roux et al. (1989) *Proc Natl Acad Sci* 86:9079-83; Snitkovsky et al. (1998) *Proc Natl Acad Sci* 95:7063-8; and Boerger et al. (1999) *Proc Natl Acad Sci* 96:9867-72, the full disclosures of which are incorporated herein by reference for all purposes. Moreover, tools for predicting the tropism of a particular virus are available, e.g., as described by Gamido et al. (2008) *J. Clin. Microbiol.* 46(3):887-891.

Upon transduction of the target cell, trans-splicing occurs between RNAs transcribed from the barcoded trans-splicing construct in the target cell and pre-mRNAs transcribed from endogenous genes in the target cell. The resulting trans-spliced fusion transcripts serve as the raw material for generating the single cell gene expression data. In certain aspects, the fusion transcripts are isolated from the transduced target cells. Suitable reagents and kits for isolating total RNA from cells are commercially available and include TRIzol® reagent (Life Technologies), RNeasy RNA purification kits (Qiagen), NucleoSpin® RNA isolation kits (Clontech) and the like. In another embodiment, the transduced cells (or a cellular extract, etc.) are inputted directly into downstream enzymatic reactions. If desired, the trans-spliced fusion transcripts isolated from the transduced target cells may be converted into cDNA via reverse transcription. Polymerases (e.g., reverse transcriptases) and other reagents (including buffers, metal cofactors, and the like) useful for reverse transcribing RNA into cDNA are commercially available. Reverse transcription kits are commercially available and include SMARTer™ cDNA synthesis kits (Clontech), QuantiTect Rev. Transcription Kit (Qiagen), SuperScript® III First-Strand Synthesis System (Life Technologies), and the like. A reverse transcription step may employ universal (random or oligo dT) primers or cDNA synthesis primers specific for trans-spliced mRNA products, e.g., complementary to the sequences of trans-splicing element.

Expression data may be generated using any suitable approach chosen by a practitioner of the subject methods for detecting and/or quantitating the trans-spliced fusion transcripts or cDNAs generated therefrom (which cDNAs are optionally amplified (e.g., by PCR) following reverse transcription). According to certain embodiments, the fusion transcripts are isolated, reverse transcribed, and PCR amplified. In certain aspects, genome-wide expression profiling is performed using a combination of trans-splicing-specific primers and universal PCR primers, or two trans-splicing-specific primers may be employed in the amplification step. A universal primer flanking an amplification cassette may be introduced in the trans-spliced mRNA or cDNA using any suitable approach, including but not limited to adaptor ligation, template-switching (e.g., using SMART™ technology by Clontech (Mountain View, Calif.) or ScriptSeq™ technology by Agilent (Santa Clara, Calif.)), tailing (e.g., using a terminal transferase), circularization (e.g., using CircLigase™ ssDNA ligase by Epicentre (Madison, Wis.)), linker ligation (e.g., using T4 RNA ligase), and/or any other suitable approach. According to one embodiment, the amplification primers incorporate specific sequences (e.g., adapter sequences) to facilitate a subsequent high-throughput (HT) sequencing step. In other aspects, the cDNA product generated after a reverse transcription step is amplified in a multiplex PCR assay (e.g., as described in the Experimental section herein). For example, the multiplex PCR may employ a mix of gene-specific primers and primer(s) specific for a trans-spliced mRNA or cDNA product. In certain aspects, the number of gene-specific PCR primers is 10 or more, 100 or more, 500 or more, or 1,000 or more, where each PCR primer is designed to target a specific sequence of one specific gene. Several multiplex primers may be designed for the same gene in order to profile different mRNA splice forms, or one primer may be designed for several distinct mRNAs to amplify mRNAs having related sequences. In certain aspects, the multiplex PCR primers include specific sequences (e.g. at the 5'-end) necessary for HT sequencing or multiplex HT sequencing.

In certain aspects, the amplification products are subjected to high throughput (HT) sequencing (e.g., using any suitable sequencing platform such as those commercially available from Illumina, Life Technologies, or the like). A single sequencing primer for sequencing the barcode element and gene-specific portion of the cDNA in a single read may be used. Alternatively, separate sequencing primers for the barcode element and gene-specific portion of the cDNA may be employed. Expression data may be generated using approaches other than HT sequencing. In certain aspects, quantitative RT-PCR (in single- or multi-plex) may be used to generate expression data, as described below in more detail. Other approaches for generating expression data may be employed, such as gene expression analysis using a hybridization assay (e.g. microarray technology (e.g., using a custom or pre-made microarray commercially available from Affymetrix, Agilent, or the like)) or nCounter® technology (NonoString Technologies, Seattle, Wash.), capillary electrophoresis-based methods, direct high-throughput sequencing of trans-spliced mRNAs or cDNAs (e.g. using HT sequencing technologies from Illumina, Inc. (San Diego, Calif.), Life Technologies (Carlsbad, Calif.), Pacific Biosciences (Menlo Park, Calif.), Helicos Biosciences (Cambridge, Mass.), etc.), or any other suitable approaches.

As described above, in certain aspects, the target cell is a diseased cell. According to one embodiment, the diseased cell is a circulating tumor cell (CTC). By "circulating tumor cell" or "CTC" is meant a cell that has shed into the vasculature from a primary tumor and circulates in the bloodstream. The circulating tumor cell may be present in a cellular sample (e.g., a biological fluid sample, such as a blood sample) obtained from a mammal (e.g., a human cancer patient) with an epithelial cell cancer, such as breast, prostate, lung, colon, or pancreatic cancer. According to one embodiment, the target mammalian cell has an epithelial mesenchymal transition (EMT) characteristic (e.g., as is displayed by certain cancer stem cells). CTCs may be obtained from a human cancer patient using any suitable approach. For example, CTCs may be captured directly in vivo using GULIPI guidewire detection/capture technology, e.g., as described in Saucedo-Zeni et al. (2012) *Int. J. Onc.* 41:1241-1250. Other suitable approaches for isolation of CTCs include ApoStream™ technology (Apocell) based upon dielectrophoresis field flow fractionation (DEP-FFF), microfiltration using the Captor™ system (Abnova), the OncoQuick™ tube-based separation system (Greiner Bio-One), the RosetteSep™ separation system (StemCell Technologies) based upon the depletion of leukocytes with CD45 antibodies, or any other technology suitable for isolating CTCs.

A method of obtaining single cell expression profiles according to one embodiment of the present disclosure is schematically illustrated in FIG. 1. In this example, the cellular sample is a heterogeneous cellular sample that includes circulating tumor cells (CTCs, the target cells) and leukocytes. The cellular sample is contacted with a packaged lentiviral barcoded trans-splicing library. For ease of illustration, five lentiviral particle members of the library are shown—each including distinct barcoded trans-splicing constructs (BC1-BC5). Three target CTCs are shown, where each CTC is transduced by a single particle member such that each CTC contains a distinct barcoded trans-splicing construct (shown in FIG. 1 as BC1, BC2 and BC3). The leukocytes in the cellular sample are recalcitrant to transduction by the lentiviral particles, and accordingly are not transduced upon contacting of the cellular sample with the library.

As shown in FIG. 1, upon transduction of a CTC by a member of the library, the barcoded trans-splicing construct (which may be integrated into the target cell genome or remain non-integrated) is transcribed (e.g., via an operably-linked promoter) to generate a barcoded trans-splicing transcript. A fusion transcript is then generated via trans-splicing between the barcoded trans-splicing transcript and an endogenous target cell pre-mRNA, mediated by a promiscuous splice acceptor site in the barcoded trans-splicing transcript and a splice donor site in the endogenous pre-mRNA. In this way, each endogenous pre-mRNA in the target cell may be labeled via trans-splicing with the barcoded trans-splicing transcripts transcribed from the barcoded trans-splicing construct. The fusion transcripts are then isolated from the cell and reverse transcribed. The resulting cDNA is amplified (e.g., PCR amplified) using primers which hybridize to sequences flanking the mRNA and barcode elements, which sequences are optionally adapter sequences added during or after reverse transcription of the fusion transcript. In this example, expression data is generated by subjecting the amplification products to high throughput (HT) sequencing. Other suitable approaches for generating the expression data are described above and include, e.g., quantitative RT-PCR (in single- or multi-plex), microarray analysis, hybridization assay, capillary electrophoresis-based methods, and the like. The subject methods may further include assigning the expression data to a specific transduced cell based on barcode identification. For example, the expression data may be clustered to each transduced cell using the unique barcode sequence of each cell. The expression data set may be unique for each transduced cell if transduction is carried out at a low MOI (e.g., less than approximately 0.5) or redundant if transduction is carried out at a high MOI (e.g., greater than approximately 0.5).

The expression data may be analyzed to determine the expression levels of one or a plurality of genes of interest. Alternatively, or additionally, the expression data (e.g., expression data generated using a HT sequencing protocol) may be analyzed for a genetic mutation. That is, the sequence of the gene-specific portion of the cDNA may be compared to a corresponding reference (e.g., wild-type) sequence to determine whether the target mammalian cell has a mutant form of the gene of interest. Mutations for which the expression data may be analyzed include one or more single nucleotide polymorphisms (SNPs), a point mutation (e.g., an amino acid substitution mutation), a genetic deletion, a genetic insertion, and any combination thereof. Once the presence or absence of a genetic mutation has been determined, this information may be traced back to the single cell from which the expression data was obtained by virtue of the distinct barcode (e.g., by clustering the data based on the barcode sequence as described in greater detail herein). In certain aspects, single-cell mutation analysis is performed in a heterogeneous cell population (e.g., cancer biopsy, CTC sample, etc.), to determine whether different cells have different mutation profiles.

According to certain embodiments, the barcoded trans-splicing constructs of the library include an effector domain. The effector domain of a given member of the library is a domain that at least includes a coding sequence for an effector of interest (which may be present in an effector cassette). Effectors of interest include, but are not limited to: nucleic acid effectors, such as deoxyribonucleic acid effectors (e.g., genomic DNA elements, genes, cDNAs for over-expression), ribonucleic acid effectors, e.g., siRNA (including siRNA, shRNA, microRNA, etc.), genetic suppression elements, non-coding RNAs, long non-coding RNAs, small RNAs and ribozymes, CRISPR RNA, deoxyribonucleic acid effectors, (e.g., antisense); polypeptide effectors, e.g., peptides, protein domains, proteins, etc., full-length proteins and the like. The effector domain may be the same in each of the barcoded trans-splicing constructs of the library, or the library may include a collection of distinct effector domains (e.g., effector nucleic acid domains) of different sequence, where the sequences of the library members have been selected based on the intended nature of the library. For example, if the constructs of the library include siRNA effector domains, an RNA target of interest is first selected, and then various siRNA sequences are selected and distinct effector sequences are designed and synthesized. The target RNA could be mRNA, microRNA, non-coding RNA, small RNA and other types of RNAs which are expressed in the target cells and could affect cellular functions. The length of a given effector nucleic acid sequence of a given effector cassette may vary, e.g., depending on the nature of the library, etc. When the construct includes an effector domain, the effector domain may be barcoded. The barcode element for the effector domain may be the same as, or distinct from, the barcode element linked to the trans-splicing element. For example, the effector domain and trans-splicing element may share a single barcode element. In other aspects, the effector domain and trans-splicing element each have a dedicated barcode element which may be of the same or different sequence. In certain aspects, a barcode element present in an effector cassette and the barcode element linked to the trans-splicing element are separate, but physically linked to each other at amplification and analysis (e.g. sequencing) steps.

In some instances, the length of the effector sequences in the library may range from 5 to 5000 nt, such as 10 to 2000 nt, including 19 to 50 nt. In certain embodiments, the effector sequences are shRNA or microRNA in which the size of the region substantially complementary to target mRNA ranges from 19 to 30 nucleotides. The number of distinct effector sequences (and therefore cassettes) of differing sequence in a given library may vary. In some instances, the number of distinct effector sequences of differing sequence is 2 or more, e.g., 5 or more, 100 or more, 1000 or more, 5000 or more, 10000 or more, 15,000 or more, 20000 or more, 25000 or more, etc. In certain embodiments, the number of distinct effector sequences of differing sequence in a given library may range from 5000 to 50000, such as 10000 to 40000 and including 20000 to 30000. Two effector sequences are considered to be distinct if their sequences differ from each other by even a single nucleotide. In a given library, each effector sequence may have the same length, or different effector members of the library may have different lengths. The effector library may include a single unique effector construct or the redundant set of effectors targeting the same cellular target (e.g. mRNA). In certain aspects, a combination of a single effector (e.g., a shRNA, CRISPR RNA, or microRNA) and a plurality of barcoded trans-splicing constructs is employed to monitor the efficacy of inactivating a specific gene product (e.g., a drug target) based on transcriptional profiling at the single-cell level. In other aspects, a plurality of barcoded effectors and a plurality of barcoded trans-splicing constructs are combined in a single viral barcoded trans-splicing library, e.g., for expression profiling used to analyze the efficacy and/or mechanism of specific gene knockdown for each effector construct present in the library.

In some instances, the barcoded trans-splicing library employed in the subject methods includes an effector domain that targets (e.g., by RNA interference), overexpresses, or ectopically expresses the key molecules important for cell functions, including but not limited to a molecule selected from the group listed at the website having an address made up of "http://" placed before and ".jsp" after cbio.mskcc.org/tcga-generanker/index, e.g.: CDKN2A; PTEN; EGFR; TP53; PIK3CA; RB1; NF1; MET; CDK4; ATM; PDGFRA; MDM2; APC; EP300; ERCC2; KRAS; PIK3CG; BRCA1; STK11; BRCA2; ERBB2; BRAF; FBXW7; MLH1; MSH2; SMAD4; CDKN2B; FGFR3; MSH6; PIK3CB; PIK3R1; ERCC3; JAK2; KIT; RET; AKT1; PLCG1; SMARCA4; CDH1; CDKN1A; DNMT1; ERBB3; NOTCH1; CCND2; MYC; NRAS; AKT2; CREBBP; NF2; NTRK1; PDGFRB; ABL1; CCND1; CDK6; HSP90AA1; TCF3; CTNNB1; FGFR1; FIGF; HRAS; NTRK3; WT1; CDC42; EXT1; FOXO3; MDM4; PDGFA; PMS2; RUNX1; VHL; WRN; ALK; AR; CDKN2C; CHEK1; CHEK2; ERCC5; FAS; FGFR2; HDAC1; KDR; NOS3; PTCH1; TERT; TSC2; BLM; CBL; COL1A1; EVI1; MAP2K4; PDGFB; SEPT9; TGFBR2; TRRAP; EGF; FLT3; GRB2; NCAM1; NOS2; BUB1B; CDKN1B; DIRAS3; DOT1L; EPHB1; EPHB6; GNAS; HIF1A; MRE11A; PLCG2; PRKDC; PTPN11; RAD50; RAD51; SPRY2; FANCA; FANCF; FGFR4; FLT1; FOXO1; MAP2K1; PPP2R1A; PTGS2; SHC1; TPO; XPA; XPC; BAI3; BARD1; BCL2; CARM1; CDK2; CERK; DGKZ; E2F1; EPHA3; EPO; ERBB4; FANCE; FH; FLT4; IRS1; MAPK1; NBN; PLCB1; PRKCZ; SMARCB1; TCF12; TPR; VEGFA; ABCC3; CD44; CDKN2D; CSF1R; DPYD; ESR2; EWSR1; FANCD2; FOS; LMO2; NOTCH3; PARP1; PRKCA; SMAD2; SMAD3; TSC1; ADCY9; AGAP2; BAX; BCL11A; BCR; BIRC5; CAV1; CCNE1; DGKB; EPHB4; ERCC6; ESR1; ETV1; FLNC; FN1; GSK3B; HDAC2; HOXA9; MEN1; MYH9; NCOA2; PCNA; PML; PPARG; PPARGC1A; RARA; SKP2; SOCS1; SOS1; SRC; TEK; TOP2A; TPM3; ABCA1; APC2; AURKA; CCND3; CD40LG; CDX2; CEBPA; CYP19A1; DNMT3B; ERCC1; ERCC4; ETV4; FES; GAB1; HGF; IFNG; IGF2R; INSR; KLF6; MPL; MUTYH; MYCL1; NR3C1; PIK3C3; PIK3CD; PIK3R2; PPP1R3A; PPP2R1B; PTPRB; RECQL4; ROS1; RPS6KA2; SDHB; SP1; THBS1; TP73; ANAPC5; ATR; BCL3; BIRC6; BRIP1; CBFA2T3; CDC73; CDK7; CLTC; CSMD3; CSNK1G2; CTNNA1; CYP1B1; DDB2; DGKI; ELOVL2; EP400I; EPHA8; EPHB2; ERG; EXT2; FANCC; FANCG; FRAP1; GATA1; GMPS; GPC3; HDAC4; HIPK2; HMGA1; HOXD11; IDH1; IGF1R; IGFBP3; KALRN; KAT2B; LAMA1; LAMP1; LDHA; LTBP1; MAPK3; MAPK8IP2; MINPP1; MLL; MLL3; MST1R; MUC1; MYST4; NAV3; NOTCH2; NSD1; PAFAH1B2; PAK7; PARP2; PIGS; POLE; PPP1R13L; PPP2CB; PPP2R2B; PTCH2; PTK2; PTPRD; RAD51L1; RHEB; RHOA; RPS6KA1; RPS6 KB1; RUNX1T1; SDHC; SDHD; SNCG; SOCS2; SPEN; TFE3; TGFBR1; TLX1; TNK2; and ZNF331. In some embodiments, the effector barcodes and trans-splicing barcodes are found in the same sequence. In other embodiments, the sequences for the effector cassette and the trans-splicing element are separated from each other, but physically linked to each other, at amplification and analysis (e.g., sequencing) steps.

In certain aspects, the subject methods further include treating the target mammalian cell (e.g., a diseased target mammalian cell) with an agent (e.g., a drug) following transduction of the cell with a member of the viral barcoded trans-splicing library. For example, in the case of cultured tumor cells (e.g., cell lines, CTCs or tumor samples), single cell expression profiles may be obtained, and the number of proliferating cells in each cellular clone with or without drug treatment may be counted. This approach would enable an investigator or clinician to correlate a particular gene expression profile of the tumor cells with responsiveness (e.g., growth inhibition) upon treatment with the drug.

Utility

The subject methods find use in a variety of different applications where, e.g., it is desirable to obtain single cell gene expression profiles from one or more cells in a cellular sample of interest. For example, the methods of the present disclosure represent a powerful approach for obtaining expression profiles on the single cell level in heterogeneous cellular samples. Such samples often exhibit a high degree of intrinsic variation in their gene/biomarker expression levels (e.g., due to the cell cycle, environment, and stochastic mechanism of transcription/translation), even among individual cells that have the same phenotype. The subject methods enable the expression profile of each cell in the sample to be interrogated individually without suffering from the low sensitivity and poor specificity of the current assays based on average profiling of cell mixes. In certain aspects, the subject methods for single-cell molecular profiling obviate the need for separating cells of interest from a heterogeneous cellular sample. As such, in some embodiments the methods do not include such a step of separating cells of interest from a heterogeneous sample of cells. Direct molecular profiling in heterogeneous cell samples is advantageous for clinical diagnostic and biomarker discovery applications. In certain aspects, methods of the present disclosure find use in molecular profiling and cellular subtyping of heterogeneous original or enriched disease tissue and biological fluid samples, e.g., biopsy tumor samples, endothelial cells from cardiovascular disease samples, bone marrow samples, lymph node samples, lymph, amniotic fluid, brain samples from different neurological disorders, lung pathological samples, and/or any other heterogeneous disease tissue sample of interest. According to certain embodiments, the methods of the present disclosure find use in the molecular profiling of normal biological tissue and biological fluid samples, to elucidate the mechanisms of differentiation, immune responses, cell-cell communication, brain development, and the like.

According to certain embodiments, the subject methods find use in obtaining single cell expression profiles in circulating tumor cells (CTCs). CTCs typically derive from metastases and can recirculate through the bloodstream and lymph to colonize distinct organs and/or the primary tumor, giving rise to secondary metastasis. CTCs play a critical role of CTCs in the metastatic spread of carcinomas. Therefore, detection of CTCs in blood ("liquid biopsy") or disseminating tumor cells (DTC) in bone marrow might be complementary to the current imaging procedures used to monitor tumor staging and would improve the identification, diagnosis and treatment of cancer patients at high risk of metastatic relapse.

In certain aspects, the methods of the present disclosure may be used to obtain expression and mutation profiles in a cellular sample that includes CTCs as well as non-target contaminating cell types (e.g., leukocytes). For example, a cellular sample obtained from blood or bone marrow that includes CTCs and leukocytes may be contacted with a packaged viral barcoded trans-splicing library as described elsewhere herein. The library may be a library (e.g., a lentiviral or adeno-associated viral library) to which the leukocytes in the sample are recalcitrant to transduction. Accordingly, the single cell expression profiles obtained from the cellular sample (via detection and/or quantitation of trans-spliced fusion transcripts mapping to individuals cells via distinct barcodes) will be almost exclusively or entirely derived from transduced CTCs. Novel CTC biomarkers which facilitate the isolation, detection, and/or monitoring of CTCs in a patient having metastatic lesions may be identified from analysis of the gene expression profiles obtained using the subject methods.

Moreover, the methods of the present disclosure are useful for identifying biomarkers of CTC subtypes. Such biomarkers may be those associated with CTCs having a metastatic epithelial mesenchymal transition/cancer stem cell ("EMT/CSC") phenotype and are presently identifiable by virtue of down-regulation of epithelial cell surface markers (e.g., EpCAM). The new biomarkers identified using the subject methods can be used for a variety of applications, e.g., to enable the isolation, detection, quantitation and/or monitoring of EMT/CSC CTCs based on biomarkers that are actually expressed by these cells, as opposed to current approaches which rely on identification of cells expressing epithelial cell surface markers. Moreover, biomarkers identified from the single CTC gene expression profiles are useful in developing diagnostics and translational research solutions for improved treatment of advanced-stage cancer patients by estimating the risk for metastatic relapse/progression, stratifying patients and monitoring the efficacy of cancer therapies, identifying therapeutic targets and resistance mechanisms, and/or creating a better understanding of the mechanisms of metastasis development.

The subject methods find use in a large variety of additional applications. For example, methods of the present disclosure find use in research and therapeutic (e.g., regenerative medicine) applications relating to human induced pluripotent stem cells (hiPSCs) and human embryonic stem cells (hESCs). Gene expression studies of hiPSCs and hESCs have revealed a globally similar pattern, with significant upregulation of key pluripotency maintenance network genes, such as Oct4 (also known as Pou5f1), Nanog, Sox2, and DNMT3B. Despite the presence of certain genetic hallmarks common to most (if not all) hiPSCs and hESCs, a population of stem cells in any given cellular sample is not a homogenous population on the molecular level. Rather, stem cells display an inherent heterogeneity at the molecular level which underlies the probabilistic nature of their fate determination.

The methods of the present disclosure may be used to generate single cell expression profiles from stem cells (e.g., hiPSCs or hESCs) present in a cellular sample of interest by contacting the sample with a packaged viral barcoded trans-splicing library as described elsewhere herein. The expression profiles obtained from the cellular sample (via detection and/or quantitation of trans-spliced fusion transcripts mapping to individuals cells via distinct barcodes) may include the expression levels of pluripotency maintenance network genes, e.g., Oct4, Nanog, Sox2, DNMT3B and/or the like. The expression of these genes may be used to confirm the presence of stem cells in the sample (e.g., a heterogeneous sample that includes cells that are not stem cells) and monitor mechanism of differentiation of these stem cells into different specialized cell lineages. Moreover, the single cell expression profiles from the stem cells in the sample may be used to identify novel biomarkers for such stem, progenitor, differentiated cells and subtypes thereof. Such novel biomarkers may be useful for improved approaches for isolating and/or characterizing stem cells, or selecting stem cells for a particular therapeutic application. The subject methods also find use in certain therapeutic applications by facilitating the assignment of hESCs and hiPSCs to "pluripotent grades" according to quantitative measurements of transcript abundance. For other therapeutic applications, the methods of the present disclosure find use in identifying the molecular signatures and selection of stem cells that have taken the initial step(s) (e.g., are fated) toward differentiating into a particular cell type of interest, such as cardiac, neuronal, or any other cell type of interest).

Reagents

Reagents, such as constructs, cells and libraries that find use in practicing the subject methods are also provided. According to one embodiment, provided is a barcoded trans-splicing construct that includes a trans-splicing element linked to a barcode element, which construct optionally further includes an effector element. The trans-splicing element, barcode element, and optional effector element may have any of the sequences/features described above with respect to the subject methods. For example, the trans-splicing element may be a spliceosome-recognized trans-splicing element (e.g., including a branchpoint, polypyrimidine tract, and a 3' splice acceptor site or 5' splice donor site). In certain aspects, the trans-splicing element is a spliceosome-recognized trans-splicing element that includes a branchpoint, a polypyrimidine tract, a 3' splice acceptor site, and a 5' splice donor site. A given trans-splicing element may include additional regulatory sequences necessary to enhance trans-splicing efficacy and promiscuity, as desired. A cell that includes a barcoded trans-splicing construct as described hereinabove is also provided. The barcoded trans-splicing construct present in the cell includes a trans-splicing element linked to a barcode element. An effector element may also be included in the barcoded trans-splicing construct present in the cell. The trans-splicing element, barcode element, and optional effector element may have any of the sequences/features described above with respect to the subject methods.

Also provided is a plurality of barcoded trans-splicing constructs, where each barcoded trans-splicing construct member of the plurality includes a trans-splicing element linked to a barcode element. According to certain embodiments, the barcoded trans-splicing construct members of the plurality further include an effector element. In certain aspects, the plurality includes a set of constructs each having a common trans-splicing element linked to a distinct barcode element. For example, the plurality may include 1000 or more (e.g., 1 million or more) barcoded transplicing constructs each having a distinct barcode element. The trans-splicing element of each member of the plurality may be a spliceosome-recognized trans-splicing element (e.g., including a branchpoint, polypyrimidine tract, and a 3' splice acceptor site or 5' splice donor site). In certain aspects, the trans-splicing element is a spliceosome-recognized trans-splicing element that includes a branchpoint, a polypyrimidine tract, a 3' splice acceptor site, and a 5' splice donor site.

A packaged viral barcoded trans-splicing library that includes a plurality of barcoded trans-splicing constructs is also provided. Each of the plurality of barcoded trans-splicing constructs includes a trans-splicing element linked to a barcode element. The plurality may include a set of constructs each having a common trans-splicing element linked to a distinct barcode element. The trans-splicing element may be a spliceosome-recognized trans-splicing element (e.g., including a branchpoint, polypyrimidine tract, and a 3' splice acceptor site or 5' splice donor site). In certain aspects, the trans-splicing element is a spliceosome-recognized trans-splicing element that includes a branchpoint, a polypyrimidine tract, a 3' splice acceptor site, and a 5' splice donor site. According to certain embodiments, the plurality includes 1000 or more (e.g., 1 million or more) barcoded trans-splicing constructs each having a distinct barcode element. The plurality of barcoded trans-splicing constructs may further include an effector element. When the constructs include an effector element, the constructs may further include a promoter operably linked to the effector elements sufficient to provide expression of the effector in transduced cells. In certain aspects, the library is a viral library. For example, the library may be a retroviral, lentiviral, adenoviral, or adeno-associated viral vector library. A population of transduced cells that includes cells transduced with any of the libraries described elsewhere herein is also provided.

Kits

Aspects of the present disclosure also include kits. The subject kits may include, e.g., reagents useful for practicing the subject methods. For example, in certain aspects, kits that include a packaged viral barcoded trans-splicing library (e.g., for transducing target cells in a cellular sample of interest) are provided. The library included in the subject kits may have any of the features described above with respect to the methods of the present disclosure. For example, the library may include a plurality of barcoded trans-splicing constructs, where a barcoded trans-splicing construct includes a trans-splicing element linked to a barcode element. In certain aspects, the plurality of barcoded trans-splicing constructs includes a set of constructs each having a distinct barcode element linked to a common trans-splicing element, e.g., a spliceosome-recognized trans-splicing element as described elsewhere herein. Alternatively, or additionally, the subject kits may include a plasmid barcoded trans-splicing library. The plasmid library may be used, e.g., to transfect a packaging cell line to produce a packaged viral barcoded trans-splicing library, which in turn may be used to transduce target cells in a cellular sample of interest to obtain single cell expression profiles according to the subject methods.

Kits of the present disclosure may include other reagents, including, e.g., transfection reagents, a packaging mix (e.g., a 2nd or 3rd generation HIV-based lentiviral or adeno-associated packaging mix), cell culture reagents, transduction reagents (e.g., reagents that enhance the infection of cells with retrovirus, such as Polybrene® or the like), control plasmids, and/or the like.

According to certain embodiments, a library or plurality of trans-splicing constructs included in the subject kits may further include an effector domain (which may be present in an effector cassette) that encodes an effector of interest, e.g., an siRNA, a CRISPR RNA, a protein, ncRNA, or the like. When the library or plurality of trans-splicing constructs includes an effector domain, the library or plurality of trans-splicing constructs may be pre-designed or custom made. By "pre-designed" is meant that the effector domains are selected by the vendor to encode effectors useful in interrogating a particular cellular pathway, diagnosing a particular disease condition, and/or the like. Pre-designed libraries or plurality of barcoded trans-splicing constructs of interest include those which permit screening of signaling pathway targets, disease associated targets, or cell surface, extracellular and DNA binding targets, for example. By "custom made" is meant the library or plurality of trans-splicing constructs includes effector domains which are selected by a purchaser of the kit.

Components of the subject kits may be present in separate containers, or multiple components may be present in a single container. For example, in kits that include a packaged viral barcoded trans-splicing library and additional transduction reagents (e.g., a transduction efficiency enhancer), the library and additional transduction reagents may be provided in separate containers, or may be provided in a single container.

In addition to the above-mentioned components, a subject kit may further include instructions for using the components of the kit, e.g., to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., portable flash drive, CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Computer Systems, Devices and Computer-Readable Media

Steps of the subject methods can be computer-implemented, such that method steps (e.g., assaying, comparing, calculating, clustering, mapping, and/or the like) are automated in whole or in part. Accordingly, the present disclosure provides computer systems, devices, computer readable media and the like in connection with computer-implemented methods of mapping and/or clustering expression data to a specific transduced cell (e.g., using the barcode element present in high throughput sequencing reads, amplification products generated during quantitative RT-PCR, or the like), determining the expression levels of a gene of interest or panel of genes of interest to generate an expression profile for that cell, and/or the like.

For example, the methods of the present disclosure may involve inputting the gene expression and/or barcode data into a computer programmed to execute an algorithm to obtain single cell expression profile data described herein, and generate a report as described herein, e.g., by displaying or printing a report to an output device at a location local or remote to the computer.

The present disclosure thus provides a computer program product including a computer-readable storage medium having a computer program stored on it. The program can, when read by a computer, execute relevant calculations based on gene expression values (e.g., relating to the identity of the gene and level of expression thereof) and barcode information obtained from analysis of one or more target cells in the cellular sample. The computer program product has stored therein a computer program for performing the calculation(s).

In certain aspects, the program is able to map and/or cluster the gene expression data (e.g., expression levels of a panel of genes of interest) to a single target cell based on the distinct barcode specific to that target cell. According to certain embodiments, when the gene expression data is obtained by nucleic acid sequencing, the sequencing data is clustered to each specific cell using the barcode sequence and then aligned with the RefSeq database using the Burrows-Wheeler Aligner program, which program is described, e.g., by Li & Durbin (2009) *Bioinformatics* 25:1754-1760. Other suitable approaches for clustering gene expression data include principal component analysis (PCA), F-statistic methods, CLIFF (CLustering via Iterative Feature Filtering), hierarchical clustering using uncentered correlation distance and centroid linkage, k-means (a partitioning method that subdivides genes into a predetermined number (k) of clusters, the self-organizing map (SOM) method, and the like, which are described, e.g., in D'haeseleer (2005) *Nature Biotechnology* 23(12):1499-1501. In certain aspects, data accumulated using the subject methods may be used to generate a reference expression profile database, which may in turn be used as a reference source for other expression profiling experiments carried out in accordance with the subject methods.

Systems for executing the program described above are also provided. The systems may include: a) a central computing environment; b) an input device, operatively connected to the computing environment, to receive gene expression data, where the gene expression data can include, e.g., sequence data that includes gene-specific and barcode-specific sequence information, as well as data indicative of the abundance of a gene expression product or panel of gene expression products of interest, and/or any other useful values obtained from an assay using the target cell(s) within the cellular sample, as described above; and c) an output device, connected to the computing environment, to provide information to a user (e.g., medical or research personnel). In certain aspects, the system further includes an algorithm executed by the central computing environment (e.g., a processor), where the algorithm is executed based on the data received by the input device, and wherein the algorithm calculates a value, which value is indicative of the biological condition of the transduced target cell. In some instances, the above describe processing component of the system is operably connected, e.g., using a wired or wireless communication protocol, to other components of a system, such as a high throughput sequencing component, e.g., a flow cell as employed in the Illumina sequencing platform, an array of pH sensitive wells having as employed in the Ion Torrent sequencing platform, etc.

Computer systems may include a processing system, which may include at least one processor or processing unit or plurality of processors, memory, at least one input device and at least one output device, coupled together via a bus or group of buses. In certain embodiments, an input device and output device can be the same device. The memory can be any form of memory device, for example, volatile or non-volatile memory, solid state storage devices, magnetic devices, etc. The processor can comprise more than one distinct processing device, for example to handle different functions within the processing system.

An input device receives input data and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data can come from different sources, for example keyboard instructions in conjunction with data received via a network.

Output devices produce or generate output data and can comprise, for example, a display device or monitor in which case output data is visual, a printer in which case output data is printed, a port for example a USB port, a peripheral component adaptor, a data transmitter or antenna such as a modem or wireless network adaptor, etc. Output data can be distinct and derived from different output devices, for example a visual display on a monitor in conjunction with data transmitted to a network. A user can view data output, or an interpretation of the data output, on, for example, a monitor or using a printer. The storage device can be any form of data or information storage means, for example, volatile or non-volatile memory, solid state storage devices, magnetic devices, etc.

In use, the processing system may be adapted to allow data or information to be stored in and/or retrieved from, via wired or wireless communication means, at least one database. The interface may allow wired and/or wireless communication between the processing unit and peripheral components that may serve a specialized purpose. In general, the processor can receive instructions as input data via input device and can display processed results or other output to a user by utilizing output device. More than one input device and/or output device can be provided. A processing system may be any suitable form of terminal, server, specialized hardware, or the like.

Computer programs (also known as programs, software, software applications, applications, components, or code) include instructions for a programmable processor, and may be implemented in a high-level procedural and/or object-oriented programming language, and/or in assembly/machine language. As used herein, the term "computer-readable medium" refers to any computer program product, apparatus and/or device (e.g., magnetic discs, optical disks, memory, etc.) used to provide machine instructions and/or data to a programmable processor, including a machine-readable medium that receives machine instructions as a machine-readable signal.

Aspects of the present disclosure may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

The following examples are offered by way of illustration and not by way of limitation.

EXPERIMENTAL

I. Development of a New Single Cell Expression Profiling System

To overcome the current shortcomings of expression profiling in hundreds to thousands of individual heterogeneous cells, a new system for obtaining a genome-wide single cell expression profile was developed. This system relies on labeling of a fraction or all transcribed pre-mRNAs that are present in each cell with a cell-specific molecular barcode by a spliceosome-mediated trans-splicing mechanism. Barcoded trans-splicing constructs consisting of a splice acceptor (SA) site to facilitate labeling of the entire population of pre-mRNAs, are delivered and expressed in a pool of target cells with lentiviral vectors. The technology does not require the isolation of individual cells. A mixture of target cells (e.g., in the range of 100-10,000 cells) is transduced with a complex lentiviral library that encodes barcoded constructs (e.g., 10 million, 1 million, or 100,000 barcoded constructs) with a promiscuous trans-splice acceptor site. Transduction is performed under conditions in which every cell receives one barcoded trans-splicing construct. To obtain the expression profile, the labeled (trans-spliced) mRNA-barcode molecules (e.g., isolated from CTCs) are reverse-transcribed, amplified and quantified by high-throughput (HT) sequencing. The HT sequencing data are then clustered to each transduced cell by the sequence of unique barcodes. The number of clusters reflects the number of transduced cells. The expression level (e.g., rate of transcription/splicing) of each trans-spliced mRNA in an individual cell is quantified by a number of reads of a mRNA-specific exonic sequence upstream of the splice-donor (5'ss) site. The sequences of trans-spliced barcoded mRNAs may be used to profile mutations, deletions, insertions, gene fusion products, and/or the like.

II. Construction of Lentiviral Barcoded Trans-Splicing Library

A complex lentiviral library that includes 25,000 barcoded constructs with a promiscuous splice acceptor site, designated the "25K BSA library", was developed by first cloning a mini-exon cassette. The cassette, shown in FIG. 2, includes a consensus branch point (BP), a polypyrimidine tract (PPT), a Splice Acceptor (or 3' ss-SA), an exonic splicing enhancer (ESE) and a splice donor (SD) site (Sheth et al. (2006) *Nucl. Acids Res.* 34:3955-3967; Warf and Berglund (2009) *Trends Biochem. Sci.* 35:169-178) between a CMV promoter and an RFP reporter. Next, downstream of the ESE element, a complex pool of approximately 10,000,000 18-nt barcode oligonucleotides with the sequence H12CH4N (wherein H is A, C or T) was cloned. The mini-exon-RFP (TRB) transcript synthesized from the CMV promoter has a stem-loop structure at the 5'-end to block specific binding of the TRB transcript to intronic sequences of pre-mRNA during the trans-splicing reaction (Kikumori et al. (2001) *Hum. Gene Therapy* 12:1429-1441; Warf and Berglund (supra)). The expression of the RFP reporter enables the number of transduced cells to be tracked and optimization of the transduction conditions.

Figure 2:
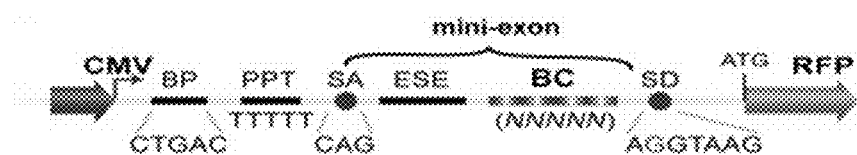
FIG. 2 schematically illustrates a barcoded trans-splicing construct according to one embodiment of the present disclosure.
Figure 3:
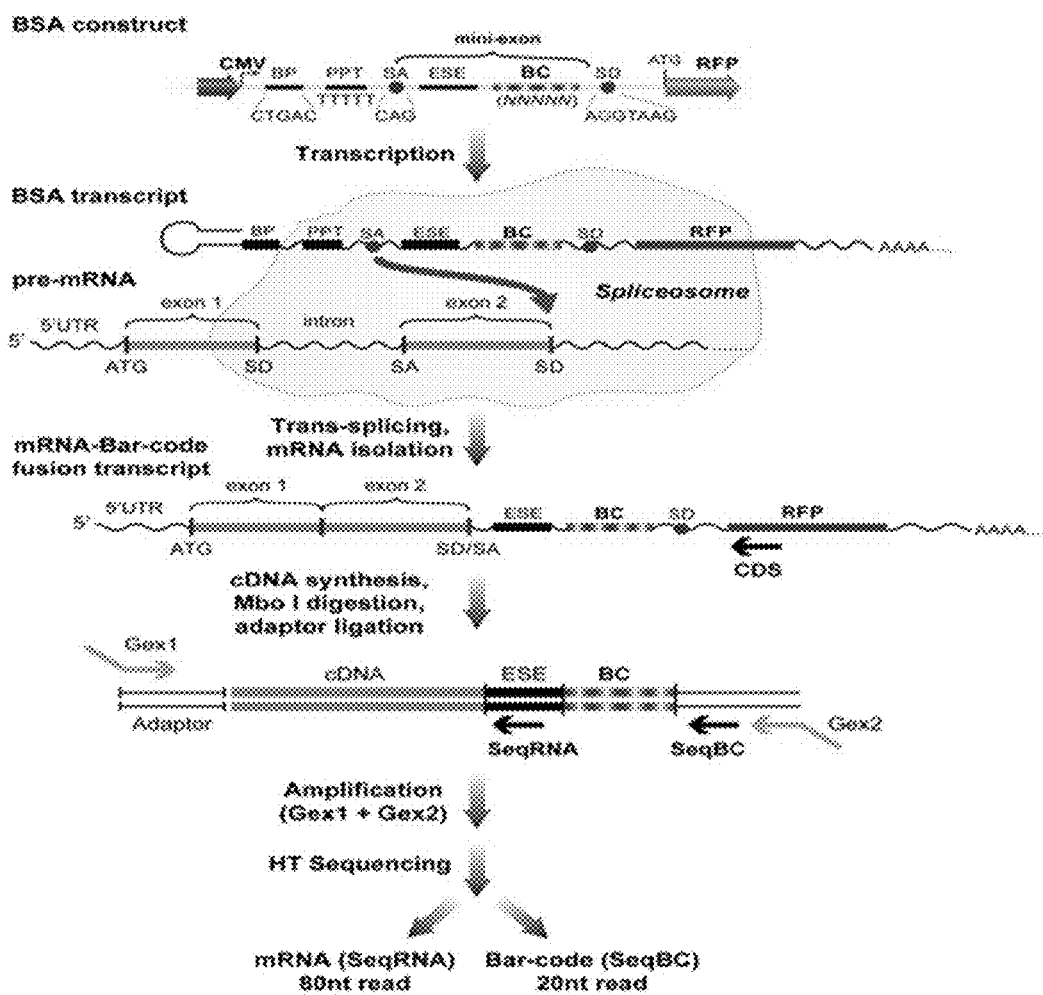
FIG. 3 schematically illustrates a use of the construct shown in FIG. 2 to generate single cell expression data according to one embodiment of the present disclosure.

FIG. 3 shows one strategy for using the barcoded trans-splicing construct shown in FIG. 2 to generate single-cell expression data. The construct (which may be integrated into the target cell genome or remain non-integrated) is transcribed to generate a barcoded trans-splicing transcript. A fusion transcript is then generated via trans-splicing between the barcoded trans-splicing transcript and an endogenous target cell pre-mRNA, mediated by the promiscuous splice acceptor site in the barcoded trans-splicing transcript and a splice donor site in the endogenous pre-mRNA. The fusion transcripts are isolated from the cell and reverse transcribed. The resulting cDNA is amplified using primers (e.g., HT sequencing-compatible Gex1 and Gex2 primers) specific to adapter sequences at the ends of the cDNA. The amplification products are then subjected to high throughput (HT) sequencing using gene-specific ("SeqRNA") and barcode-specific ("SeqBC") sequencing primers. A single sequencing primer configured to sequence the barcode and the gene-specific portion of the cDNA in a single sequencing read (rather than two separate primers for two separate reads) may be also employed.

III. Transduction and Expression Analysis in HEK293 Cells

To perform expression profiling at a single-cell level, the 10 M BSA library was packaged and transduced in 10,000

HEK293 cells at an MOI=0.2 (approximately 2,000 transduced cells). The cells were grown for 7 divisions to obtain approximately 100 cells (clones) from each transduced cell in order to reduce stochastic noise in the single-cell expression data. The total RNA was purified using a DNA-free RNeasy™ kit (Qiagen), reverse-transcribed with SuperScript® III reverse transcriptase (Invitrogen) at 50° C. using a BSA-specific CDS primer, and followed by second-strand synthesis that initiated by adding Hybridase™ RNase H (Epicentre) at 50° C., followed by MboI digestion of synthesized ds cDNA. MboI-digested cDNA was ligated with an Mbo-adaptor, and the adaptor-ligated cDNA-barcode cassette was amplified by Phusion® DNA polymerase (Finnzymes) using Gex1 and Gex2 primers (see FIG. 3). The amplified cDNA-barcode cassette was purified in a 3% agarose gel (fragments 200-400 bp) and sequenced in an Illumina HiSeq 2500 machine (150,000,000 reads per sample) using SeqBC (20-nt read) and SeqRNA (80-nt read) primers. As a control, total RNA samples isolated from HEK293 cells and HEK293 cells transduced with the 10 M BSA library were used to generate the reference expression profile using the conventional Affymetrix U133+2 chip.

Figure 5:
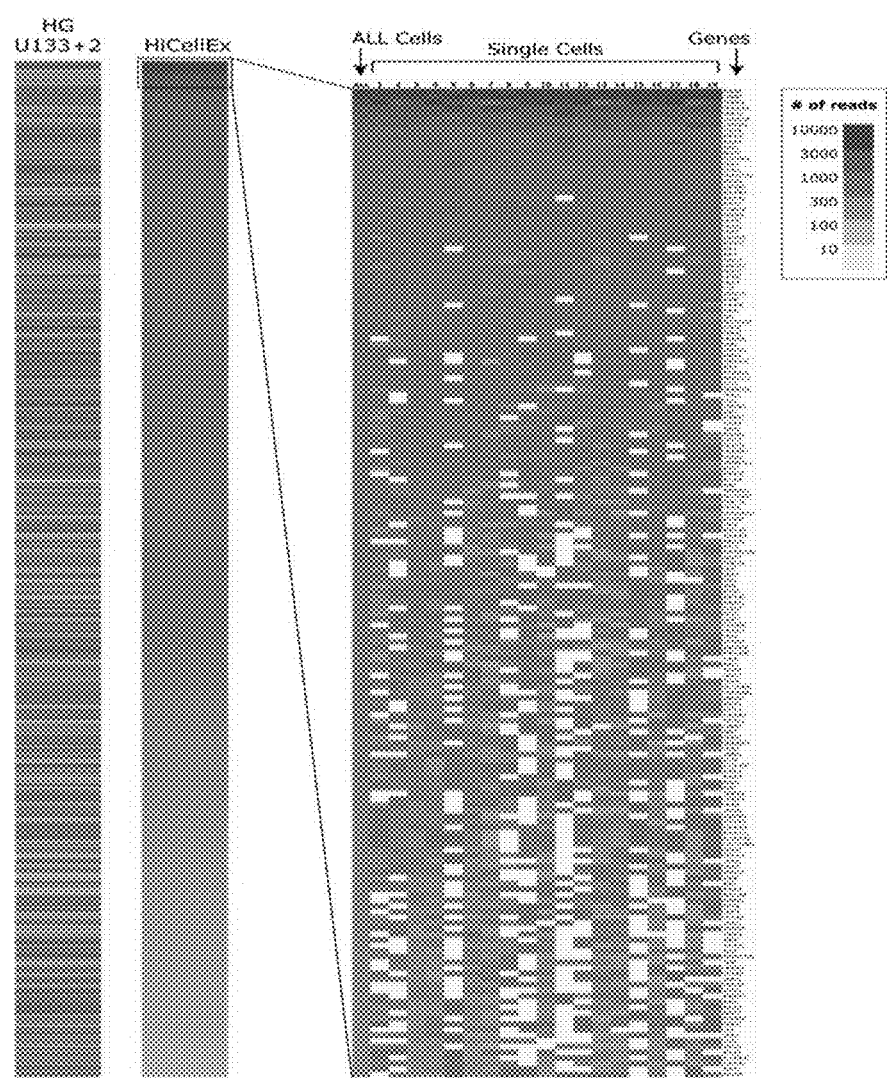
FIG. 5 shows a comparison of Affymetrix HG133+2 expression profiling data and HiCellex expression profiling data obtained using a method according to one embodiment of the present disclosure (HiCellex) for pooled 2,000 HEK293 cells/clones based on the 1,600 top genes revealed by HiCellex assay. Also shown (on the right) is stochastic noise in the top 170 gene expression profiles for the 20 random single-cells (clones).

FIG. 5 shows the comparison and overlap between the approximately 1,600 top transcripts identified using the 10 M BSA library/sequencing and the conventional (Affymetrix U133+2 array) expression profiling approach. In spite of the fact that the 10 M BSA library/sequencing assay primarily measures the rate of transcription/splicing rather than the steady-state level of the mRNA in the cell, there was significant overlap (approximately 80%) in the number of abundant transcripts identified by the 10 M BSA library/sequencing and Affymetrix expression profiling technologies. These results indicate that the BSA library technology is capable of generating single cell expression profiles on a genome-wide scale.

Furthermore, to confirm that the assay could be used for genome-wide profiling at the single-cell level, we compared the expression profiles for approximately 2,000 cellular clones derived from single transduced cells. As shown in FIG. 5 (right), significant biases in the expression profiles between different clones of HEK293 cells transduced with the 10 M BSA library were not observed.

IV. Molecular Profiling in a Heterogeneous Cell Population

Molecular profiling of heterogeneous circulating tumor cells (CTCs) is critical to identify and reveal the role of different CTC subpopulations in metastatic cancer progression and treatment response. Described herein is the development of a high-throughput (HT) technology for genome-wide expression analysis/profiling of hundreds to thousands of epithelial cancer cells at the single cell level in a background of contaminating leukocytes. The developed genetic profiling technology does not require cell separation in the CTC sample. Rather, it is based on the labeling of mRNAs in the individual cancer cells with unique cell-specific molecular barcodes, amplification of barcoded cDNAs, and analysis of gene expression in every cell by HT sequencing.

Figure 6:
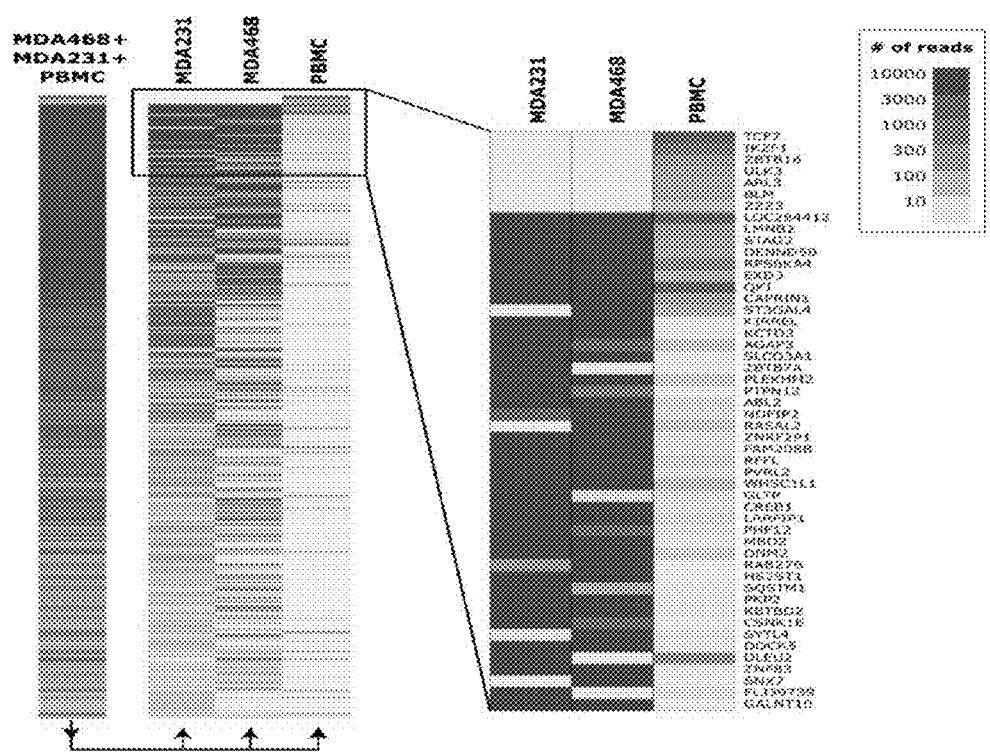
FIG. 6 shows expression profiling data from a heterogeneous cell population.

As a model system for the molecular profiling of heterogeneous cell populations, a genome-wide assay at the single-cell level in pure MDA231 (Basal A), MDA468 (Basal B) cells, PBMCs (isolated from healthy donor blood) or a mixture of all three cell types (at a 1:1:1 ratio), was performed. To mimic a CTC sample, the cells were grown and infected in suspension. Specifically, 3,000 cells of each type or the mixture (3,000 cells of each type) were transduced with an equal amount of the 10 M BSA library at an MOI=0.3 (for MDA231 and MDA468). Total RNA was isolated 12 hours after transduction. Following reverse transcription of the RNA, single cell expression profiles were generated as described above in the HEK293 studies. Under these conditions, the transduction efficiency of the PBMCs was at least 20-fold less than that for MDA231 and MDA468 cells, estimated by the percentage of RFP-positive cells. As a result of the low transduction efficiency, the PBMCs did not generate a significant amount of expression data which could interfere with analysis of the MDA profiling data. As shown in FIG. 6, hierarchical cluster analysis of single-cell expression profiling data of the cell mixture allowed discrimination between the specific signatures for MDA231 cells, MDA468 cells, and PBMCs. Moreover, the difference between the two breast cancer cell lines, MDA231 and MDA468, was significantly higher than the level of stochastic noise between the different individual cells of the same phenotype in accordance with previously published single-cell profiling studies (Goetz & Trimarchi (2012) Nature Biotech. 30:763-764; Ramskold et al. (2012) Nature Biotechnol. 30:777-783).

V. Multiplex Quantitative RT-PCR Assay

Figure 7:
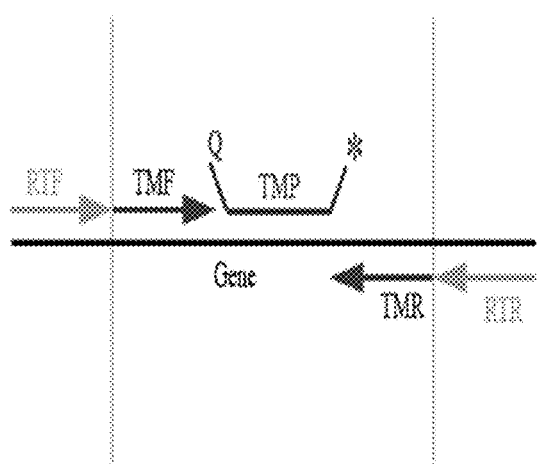
FIG. 7, Panel A schematically illustrates a multiplex quantitative RT-PCR (Q-RT-PCR) assay according to one embodiment of the present disclosure.
Figure 7:
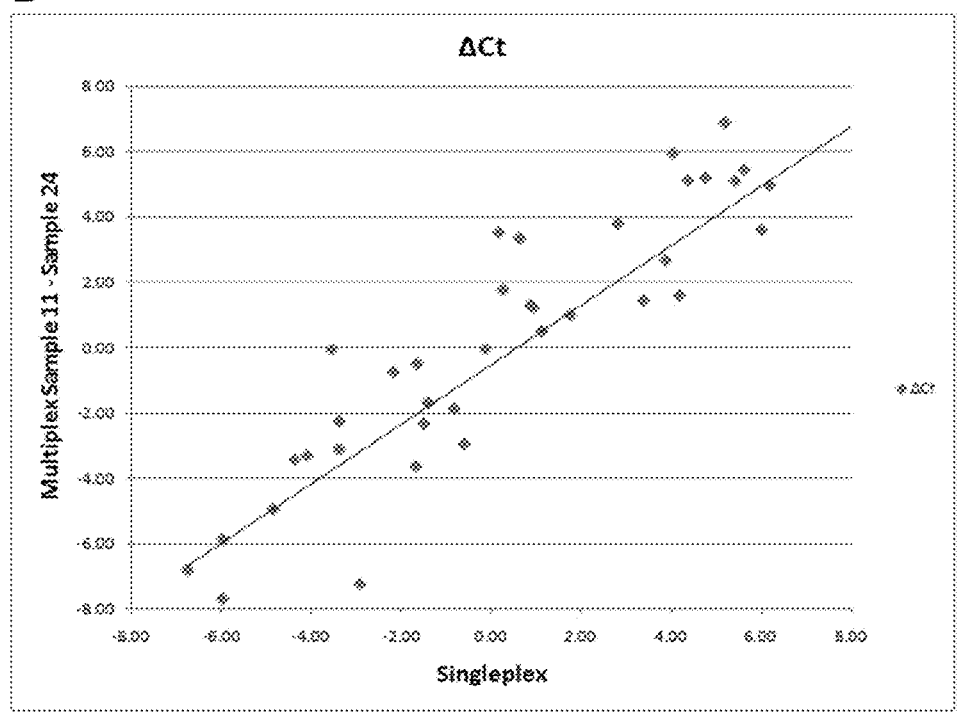

A multiplex quantitative RT-PCR (qRT-PCR) assay was developed and may be employed to generate single cell expression profile data when practicing the subject methods described above. The qRT-PCR assay is capable accurate quantitation of approximately 750 genes simultaneously in 2 pg of total RNA isolated from heterogeneous cell samples. Moreover, there was no skewing of their representation. According to the developed protocol, first-strand synthesis is performed on total RNA using random hexamer primers. The resulting cDNA is pre-amplified in a high multiplex reaction using 750 gene-specific primers sets (RTF+RTR) (FIG. 7, Panel A). Next, pre-amplified cDNA is aliquoted into individual wells of a 384-well plate and the level of each gene transcript is quantified individually via conventional qPCR TaqMan® assays (using gene-specific TMF+TMR primers and TMP probe). To assess the performance of the multiplex qRT-PCR, the expression levels of 48 genes was measured in cDNA that was pre-amplified in high multiplex PCR with 750 gene-specific primer sets. As a control, we performed qPCR quantification of mRNA transcripts on non-amplified cDNA (singleplex format). The result of this experiment, shown in FIG. 7, Panel B, demonstrates that the qRT-PCR assay allows unbiased linear amplification of up to 750 mRNAs.

VI. Development of a 500 Metastatic Gene Signature (MGS) Breast Assay

As a first step in characterizing heterogeneous populations of CTCs in breast cancer patients, reference genome-wide expression profiles at the single-cell level (for 1,000 cells) will be generated using the subject methods (e.g., using the technology shown in FIGS. 1-3) in a subset of metastatic cell lines with different phenotypes (Basal A, Basal B and Luminal subtypes) that are selected from a well-characterized 45 ATCC Breast Cancer Cell Panel (Neve et al. (2006) Cancer Cell 10:515-527; Kao et al. (2009) PLoS ONE 4:e6146; www.atcc.org/CulturesandProducts/CellBiology/KitsPanels/TumorCellPanels/TissueSpecificTumorCell-Panes/BreastCancerCellPanel/tabid/1770/Default.aspx).

To generate reference genome-wide expression profiles, 15 reference breast cancer cell lines, control normal HMECs, and PBMCs isolated from the blood of healthy donors (100,000 cells each) was transduced (at MOI=0.5) with the 27K U7 BSA non-integrated lentiviral library. The 27K U7 BSA library has the structure bGHpolyA-mU7p-SA-27 kBC22, where bGHpolyA is a bovine growth hormone polyadenylation site, mU7p is a mouse U7 promoter with downstream sequence of the mouse U7 snRNA and downstream termination sequences. Mouse U7 snRNA sequence (see Meyer, K. & Schümperli, D. (2012) Antisense Derivatives of U7 Small Nuclear RNA as Modulators of Pre-mRNA Splicing, in Alternative pre-mRNA Splicing: Theory and Protocols (eds S. Stamm, C. W. J. Smith and R. Lührmann), Wiley-VCH Verlag GmbH & Co. KGaA, Weinheim, Germany) was modified to incorporate splice acceptor element followed by 22-nucleotide barcode with stem-loop structure and sequence N22-TATT-N22 and Sm protein complex binding site. The transduced cells were incubated for 24 hours in growth media, and total RNA was purified using a DNA-free RNeasy™ kit (Qiagen). Based on the results of preliminary studies, 24 hours of cell growth is sufficient for the integration, expression and promiscuous trans-splicing of lentiviral barcoded trans-splicing constructs with pre-mRNAs in the spliceosome. After isolation, the mRNA-barcoded fusion trans-spliced transcripts were reverse-transcribed with the CDS primer, and double-stranded cDNAs were digested with the MboI and Tail enzymes and ligated with the MboI or Tail adapter. Barcoded cDNA fragments were amplified using adaptor (Gex1) and TSA construct-specific (Gex2) primers. Amplified cDNA-BC samples were cloned in a TA cloning vector and analyzed for the percentage of correct trans-spliced products. The cDNA-BC samples, which contain at least 50% of the trans-spliced molecules, were sequenced on a HiSeq2500 machine (Illumina) with approximately 150 M reads (1 lane) per RNA sample. The HT sequencing data were aligned with the RefSeq database using the Burrows-Wheeler Aligner program (Li & Durbin (2009) *Bioinformatics* 25:1754-1760). With a total of 150 M reads, most of the expressed genes were identified in a 10,000-fold dynamic range for each cell line. A subset of 300,000 reads per transduced cell permitted adequate to measure the variability in the mRNA single-cell level of the most expressed genes in a 100-fold dynamic range. For gene expression variability analysis, the total number of reads for each cell was normalized to 300,000, and the digital expression value for each gene was normalized against the mean of the reference panel of housekeeping genes (UBB, ACTB and GAPDH) as described by Powell et al. (2012) *PLoS ONE* 7:e33788. Statistical analysis of digital expression data in triplicate samples was performed using a modified version of the public R-based statistical package (www.r-project.org.)

TABLE 1

15 Reference Breast Cancer Cell Lines

| Cell Line | Markers | Tumor Type | Source |
|---|---|---|---|
| Basal B Subtype | | | |
| HCC38 | ER−, PR−, ALDH1+++, TP533m++ | DC | PB |
| MDA231 | ER−, PR−, ALDH1+/−, CD24−, CD44+++, TP53m++ | AC | PE |
| MDA157 | ER−, PR−, ALDH1+, TP53− | MC | PE |
| HS578T | ER−, PR−, ALDH1+/−, CD24−, CD44+++, TP53m+ | ILC | PB |
| MCF10A | ER−, PR−, ALDH1+/−, TP53wt+/− | F | PB |
| Basal A Subtype | | | |
| BT20 | ER−, PR−, ALDH1+/−, CD24−, CD44+++, TP53wt++ | ILC | PB |
| HCC1954 | HER+, ER−, PR−, ALDH1+, TP53+/− | DC | PB |
| MDA468 | ER−, PR−, CD24+/−, CD44++, TP53+ | AC | PE |
| HCC1937 | ER−, PR−, ALDH1+, CD24+/−, CD44+, TP53− | DC | PB |
| HCCI569 | HER+, ER−, PR−, TP53m− | MC | PB |
| Luminal Subtype | | | |
| SKBR3 | HER+, ER−, ALDH1+++, CD24+, CD44+/−, TP53+ | AC | PE |
| MCF7 | ER+, PR+, ALDH1+/−, TP53wt+/− | ILC | PE |
| T47D | ER+, PR+, ALDH1−, TP53m++ | ILC | PE |
| MDA453 | ER−, PR−, ALDH1+, CD24+/−, CD44−, TP53wt− | AC | PF |
| ZR7530 | HER+, ER+, PR−, ALDH1−, TP53wt− | ILC | AF |

Table 1. List of the reference breast cancer cell lines with Basal A, Basal B and Luminal subtypes proposed for Phase I studies.
AC - adenocarcinoma,
ILC - invasive lobular carcinoma,
MC - metaplastic carcinoma,
F - fibrocystic disease,
DC - ductal carcinoma.
PB - primary breast,
PE - pleural effusion,
PF - pleural fluid,
AF - ascites fluid.
ER - estrogen receptor,
PR - progesterone receptor,
HER - ERBB2 receptor,
ALDH1 - aldehyde dehydrogenase 1,
TP53 - p53.

The compendium of genome-wide single-cell expression profiles obtained from the breast cancer cell line panel will be analyzed to select a subset of the most informative genes for subtyping and molecular profiling of the metastatic properties of breast cancer cells. The primary goal of this step is to exclude genes that cannot be effectively used in the assay. Another goal is to select approximately 500 of the most informative subtyping and metastatic signature (MGS) genes, which can be further used for profiling CTCs. To accomplish these objectives, genes that meet the following two criteria will first be selected: 1) a high level of expression in at least 2 cancer cell lines; and 2) clear discrimination between different cancer cell subtypes (Basal A, Basal B, Luminal, and control HMECs and PBMCs) with low variation (less than 10-fold) at the single-cell level. Then, from among the genes that meet the above minimal criteria for the robust assay, we will choose genes that overlap with: 1) commercial prognostic breast cancer gene signatures: the 21-gene Oncotype DX® (Genomic Health), the 70-gene MammaPrint (Agendia), and the 76-gene Rotterdam signature; 2) the PAM50 prognostic and tumor subtyping gene signature; 3) individual genes that are present in at least 2 of 38 published metastatic, EMT, and stem cell signatures, consisting of a total of 1,500 genes ("http://" placed before and ".jsp" placed after compbio.dfci.harvard.edu/genesigdb/index); 4) drug targets for breast cancer-targeted therapeutics that are FDA-approved and in clinical trials (e.g., ERBB2, EGFR, PDGFR, etc.) ("http://www." placed before and ".ca/" placed after drugbank; Therapeutic Target Database: "http://" placed before and "ttd.asp" placed after xin.cz3.nus.edu.sg/group/ttd/); 5) a list of genes (approximately 60) with the most significant (driver) mutations and DNA copy number changes from the breast Cancer Genome Atlas Network project; and 6) epithelial, EMT, stem cell markers (approximately 50) and control genes (e.g., CD45, CD16, ACTB, UBB) that are commonly used for molecular profiling of CTCs (Ignatiadis et al. (2012) Recent Results in Cancer Research vol. 195; Lianidou & Markou (2011) Clin. Chem. 57:1242-1255).

To develop the 500 MGS assay, a set of RNAse H-dependent forward PCR primers will be designed and synthesized for the approximately 500 selected MGS genes. Furthermore, using the set of 2-3 trans-spliced cDNA samples (generated from 15 breast cancer cell lines transduced with the 27K U7 BSA library) 500 selected exon-barcode sequences will be amplified using a mixture of 500 MGS primers and the BSA library vector-specific Gex2 primer. The amplified products will be analyzed by HT sequencing. PCR primers that generate a significant amount of non-specific products or a low yield of gene-specific products will be redesigned and tested until a complete set of reliable primers for the 500 MGS assay is obtained.

The optimized 500 MGS multiplex assay will be employed to generate expression profiles using 15 breast cancer cell lines and control cells (1,000 cells each). Each multiplex assay will be run in triplicate (each triplicate with a different indexing Gex2 primer) to measure the reproducibility of expression measurement. It is expected that data analysis will allow discrimination between all subtypes (Luminal, Basal A, Basal B and control cells) and individual cell lines in each subtype and characterize the intrinsic heterogeneity, including the EMT/CSC subpopulation, in all 15 breast cancer cell lines. Additional experiments will be performed with mixtures of the 10 most phenotypically different cancer cell lines (a total of 1,000 cells mixed in the 1/1 to 1/100-ratio range) in the presence of 1,000 PBMCs to characterize the sensitivity (up to the single-cell level), reproducibility and accuracy of basal A, basal B and luminal A cell subtyping.

VII. Development of pRTS Lentiviral Trans-Splicing Vectors

In order to develop lentiviral vectors applicable for single-cell expression profiling, the basic shRNA expression vector pRSI16 developed by Cellecta for RNAi genetic screening was modified. The third-generation pRSI16 lentiviral vector with the structure 5'RSV-LTR-GAG-RRE-U6-cPPT-UbiC-tagRFP-2A-Puro-WPRE-3' dLTR was modified to develop pRTS vectors for easy cloning of a TSA (trans-splicing acceptor) cassette: 5'RSV-LTR-GAG-RRE-U6-cPPT-CMV-(XbaI/NheI)tagRFP-WPRE-3' dLTR, where 5'RSV-LTR, GAG-RRE, cPPT, 3' dLTR are lentiviral vector elements known in the art necessary for transcription, packaging, transduction, and integration of pRTS lentiviral constructs in the target cells. Another version, the pRTS21 lentiviral vector having increased promiscuous trans-splicing efficiency has the following structure: 5'RSV-LTR-GAG-RRE-bGHpolyA-cPPT-CMV-BbsI/BbsI-3' dLTR, wherein bGH-polyA is a polyadenylation signal and BpiI/BpiI cloning sites are designed for cloning splice acceptor-barcode element downstream of CMV promoter. Another version, the pRTS28 lentiviral vector, has the structure 5'RSV-LTR-GAG-RRE-bGHpolyA-cPPT-mU7p-BbsI/BbsI-mU7snRNA-3' dLTR and was developed for cloning and expression of a barcoded splice acceptor cassette from a mouse U7 promoter in the backbone of a U7 snRNA. The packaging step usually requires transduction of pRTS vector with a mix of packaging plasmids known in the art which encode additional viral proteins necessary for packaging, transduction and integration of pRTS construct. In one embodiment, the pRTS vector was packaged in the pseudoviral particles with packaging plasmid encoding a defective integrase gene (available from Life Technologies, Carlsbad, Calif.). The integration-defective pRTS pseudoviral particle could effectively transduce a target cell, replicate and express TSA effector construct in the nucleus without integration in genomic DNA. In another embodiment, pRTS vector could incorporate a cassette necessary for replication of non-integrated pRTS vector in the transduced cells, e.g. such as an SV40 origin of replication. The replicative pRTS vectors are useful to increase concentration and long-term expression of expressed TSA constructs. In an additional embodiment, the lentiviral integration system is modified in order to provide specific integration of pRTS vectors at a specific chromosomal location, rather than non-specific integration of conventional lentivectors in transcriptionally active chromosomal locations. Increased specificity of integration can be achieved by, e.g. modification of lentiviral integrase.

The U6 promoter is an optional RNA-polymerase III promoter for expression of an shRNA effector. We also employed U6 promoter for expression of TSA constructs but find that U6-TSA constructs are less effective in trans-splicing than constructs expressed from CMV promoter. Other RNA polymerase III promoters (e.g. H1, tRNA, etc.) or an RNA polymerase II promoter can be employed instead of the U6 promoter for expression of an effector or TSA construct.

The CMV promoter is used for expression of the trans-splicing acceptor. A strong CMV promoter can be replaced for any constitutive promoter (e.g. UbiC, PGK, EF1, U7, etc.), or promoters which can be regulated by external stimulus (e.g. Tet-CMV, regulated by doxocycline) or cell-type-specific promoter which is active in a specific cell type (e.g. an Oct4 promoter, which is active in stem cells). The pRTS vector may include two different promoters (e.g. mU7 and hU7, CMV and mU7, UbiC and mU7, etc) for expression of two different barcoded trans-splicing RNAs.

XbaI and NheI sites were used for cloning the TSA construct, but any other specific restriction or recombination sites (e.g. two BbsI sites) can be employed for cloning the splice acceptor or splice donor cassette.

The tagRFP gene encodes a fluorescent reporter protein (Evrogen, Moscow, Russia). Other reporter proteins or combination of reporter proteins can be employed in pRTS vectors (e.g. other fluorescent, luminescent, drug resistant, cell surface, etc. proteins). Of interest are cell surface proteins (e.g. H2Kk, truncated NGFR, etc.) proteins which can be employed for isolation of cells (e.g. with antibody-labeled magnetic beads—Miltenyi Biotech) transduced with pRTS constructs.

An additional element useful for pRTS vectors (and AAV-TS vectors described below) is a poly-adenylation (polyA+)site, which can be placed upstream of the CMV promoter. PolyA+ elements are known in the art and include the bovine growth hormone bGH polyA+, or SV40 polyA+, etc. elements cloned upstream of CMV promoter (or instead of cPPT for AAV-TS vectors) to reduce undesirable inter-splicing between any SD site located upstream of CMV promoter and SA site in TSA cassette cloned under control of CMV promoter.

A wild-type CMV promoter (flanked with BstBI and XbaI restriction sites, +1—transcriptional start site, ATG—tagRFP translation start codon) in the basic pRTS2 vector is shown in FIG. 8, Panel A (SEQ ID NO:1). The TSA4 splice acceptor construct, which was cloned into the vector between the XbaI and NheI sites is shown in FIG. 8, Panel B (SEQ ID NO:2). The TSA4 construct includes consensus elements necessary for trans-splicing (BP—branch point, PPT—poly-pyrimidine tract, and SA—splice acceptor (or 3' splice-site)). Np9, Gex2M, GexSeqS are primers for amplification and sequencing of trans-spliced mRNA-TSA fusion RNAs. A transcript transcribed from the CMV promoter has a structure at its 5' end as shown in FIG. 8, Panel C (SEQ ID NO:3) (where 5' CAP refers to the mRNA CAP structure).

The TSA4 transcript has a sequence upstream of the branch point which could potentially interact with pre-mRNA and reduce efficacy of non-specific of trans-splicing with different pre-mRNAs in the cell. In order to reduce the mRNA-specific trans-splicing, we developed a TSA16 cassette (cloned between XbaI and NheI sites in CMV promoter) which includes self-complementary sequences for blocking specific trans-splicing as shown in FIG. 8, Panel D (SEQ ID NO:4). The self-complementary sequences are underlined, ESE1 is an exonic splicing enhancer, and Bpi sites are for cloning the barcode cassette.

In another embodiment, in order to increase promiscuity of trans-splicing, we modified and developed the CMVd2M promoter shown in FIG. 8, Panel E (SEQ ID NO:5), where an XbaI cloning site is located just upstream of the transcriptional start site (+1). The CMVd2M promoter also has several mutations (shown in red), which eliminate weak splice donor SD sites, inducing non-specific inter-splicing (between the SD and SA in TSA cassette) in transcripts synthesized from any promoter upstream of CMVd2M promoter (e.g. after integration at a transcriptionally active chromosomal location). The CMVd2M promoter allows cloning of the TSA cassette without additional extended sequences upstream of BP site, e.g. the TSA9 cassette shown in FIG. 8, Panel F (SEQ ID NO:6), where ESE5 is an exonic splicing enhancer, and +1 is the transcriptional start site.

In another embodiment, the stem-loop structure was employed at the 5'-end of TSA RNA in order to block specific interaction with pre-mRNAs, as shown in FIG. 8, Panel G (SEQ ID NO:7) (TSA18 construct), where self-complementary sequences in stem-loop structure are underlined.

In order to increase the efficiency of the trans-splicing reaction, we developed TSA cassettes with an additional SD site (TSA18-SD and TSA19-SD) to mimic mini-exon structure, or with additional SD and SA sites (TSA18-SD-SA). The TSA18-SD construct, where the SD site is located upstream of the NheI site, is shown in FIG. 8, Panel H (SEQ ID NO:8). The TSA19-SD construct is shown in FIG. 8, Panel I (SEQ ID NO:9) and includes the SD site located downstream of a second BpiI site and allows identification of two different TSA constructs, which can trans-splice to each other, by HT sequencing using a primer complementary to the ESE5 sequence. The TSA18-SD-SA construct, where an additional SA cassette (BP-PPT-SA) is located downstream of the SD site, is shown in FIG. 8, Panel J (SEQ ID NO:10).

The developed TSA cassettes were employed for cloning clonal bar-code cassettes. One example of a clonal barcode cassette is an 18-nt CB18H cassette which can be cloned between two BpiI sites as shown in FIG. 8, Panel K (SEQ ID NO:11) (where H=A,C,T; N=A,G,C,T; and D=G,A,T).

In another embodiment, we employed a 90K-CB18 clonal barcode cassette, which is a mix of approximately 90,000 specific barcodes designed without significant secondary structures, balanced GC content (approximately 50%) and palindromic sequences.

Additional lentiviral vectors (pRTS21, pRTS28) and corresponding splice acceptor cassettes are shown in FIG. 8. Lentiviral vector pRTS21 is shown in FIG. 8, Panel L (SEQ ID NO:12). Lentiviral vector pRTS28 is shown in FIG. 8, Panel M (SEQ ID NO:13).

The design of the oligo pool for construction of 27K BSA libraries with 22-nucleotide clonal barcodes with stem-loop structure are shown in FIG. 8, Panel R (SEQ ID NO:18). Hairpin CB20 (shown in italics) permits clonal barcode cassettes having 27,000 different barcodes. Underlined sites are for cloning of 27k-CB-IND9 cassette in a TSA construct after amplification and digestion of PCR product with BSAI. iND9 is a sequence for binding of primers for cDNA synthesis and PCR amplification.

VIII. Development of Adeno-Associated Virus Trans-Splicing (AAV-TS) Vectors

TSA cassettes developed and validated for pRTS vectors were used for cloning in AAV vectors. The resulting AAV-TS vectors have the following features: 5'ITR-U6-PolyA1-CMV-TSA-tagRFP-PolyA2-ITR3', 5'ITR-PolyA1-CMV-TSA-PolyA2-ITR3', or 5'ITR-PolyA1-mU7p-TSA-tagRFP-PolyA2-ITR3'.

5'ITR and ITR3' are AAV inverted terminal repeats, necessary for packaging, transduction and replication of AAV-TS constructs in the target cells. In one embodiment, the AAV vector is an scAAV vector, which has deletions or mutations in the 5'ITR and form double-stranded AAV DNA in the transduced cells without replication.

PolyA1 and PolyA2 are polyadenylation signals necessary to terminate transcription from the CMV promoter or any promoter upstream of the CMV promoter and reduce inter-splicing reactions with TSA transcripts. In one embodiment, polyA1 and polyA2 signals are different. Use of the polyA1 signal is optional.

The U6 promoter is an optional RNA-polymerase III promoter for expression of an shRNA effector. We also employed the U6 promoter for expression of TSA constructs but find that U6-TSA constructs are less effective in trans-splicing than constructs expressed from CMV promoter. Other RNA polymerase III promoters (e.g. H1, tRNA, etc.)

or an RNA polymerase II promoter can be employed instead of the U6 promoter for expression of an effector or TSA construct.

CMV, mU7p, TSA and tagRFP cassettes are the sequences of CMV and mU7 promoters, trans-splicing acceptor cassettes and reporter gene as described above for pRTS vectors.

A first example AAV-based viral vector (pscAAV5) for cloning of TSA-clonal barcode cassettes is shown in FIG. 8, Panel N (SEQ ID NO:14). In this example, the TSA cassette is cloned in BpiI/BpiI sites, followed by cloning of clonal barcode cassette in BpiI/BpiI sites of the TSA insert. The resulting TSA-barcode cassette is expressed from a CMV promoter. A second example AAV-based viral vector (pscAAV6) for cloning of TSA-clonal barcode cassettes is shown in FIG. 8, Panel O (SEQ ID NO:15). In this example, the TSA cassette is cloned in BpiI/BpiI sites, followed by cloning of clonal barcode cassette in BpiI/BpiI sites of the TSA insert. The resulting TSA-barcode cassette is expressed from a U7 promoter.

An example of a TSA cassette (mU7-SA6Es-IND9) for cloning in BpiI/BpiI sites of the pRTS28 and pscAAV6 vectors is shown in FIG. 8, Panel P (SEQ ID NO:16). A second example of a TSA cassette (CMV-SA6GE12MS) for cloning in BpiI/BpiI sites of the pRTS28 and pscAAV6 vectors is shown in FIG. 8, Panel Q (SEQ ID NO:17). Flanking cloning sites are underlined. BP=branch point; PPT=polypyrimidine tract; SA=splice acceptor site; ESE6=exonic splice enhancer; Sm=binding site for Sm protein; U2snRNA comp=sequence complementary to U2 snRNA; BpiI/BpiI sites are for cloning the clonal barcode cassette.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of obtaining a single cell expression profile from a target mammalian cell, the method comprising:
   contacting a cellular sample comprising the target mammalian cell with a packaged viral barcoded trans-splicing library comprising a plurality of barcoded trans-splicing constructs under transduction conditions, wherein a barcoded trans-splicing construct comprises a trans-splicing element linked to a barcode element and the plurality of barcoded trans-splicing constructs comprises a set of constructs each having a distinct barcode element linked to a common trans-splicing element that is a spliceosome-recognized trans-splicing element comprising a splice acceptor site; and
   generating expression data from the resultant transduced target mammalian cell to obtain the single cell expression profile from the target mammalian cell, wherein the single cell expression profile comprises the expression level of 50 or more genes of interest.

2. The method according to claim 1, wherein the splice acceptor site comprises a branchpoint, a polypyrimidine tract and a 3' splice site.

3. The method according to claim 1, wherein the trans-splicing element is a spliceosome-recognized trans-splicing element comprising a splice acceptor site and a splice donor site.

4. The method according to claim 1, wherein the barcoded trans-splicing construct comprises a promoter operably linked to the barcoded trans-splicing element, which promoter is configured to provide expression of the barcoded trans-splicing element upon transduction of the target mammalian cell.

5. The method according to claim 1, wherein the barcoded trans-splicing library has a complexity that is greater than the number of transduced cells.

6. The method according to claim 5, wherein the complexity of the barcoded trans-splicing library is 5-fold or greater than the number of transduced cells.

7. The method according to claim 1, wherein the barcoded trans-splicing library comprises 1000 or more barcoded trans-splicing constructs each having a distinct barcode element.

8. The method according to claim 1, wherein the expression data is generated using a high-throughput sequencing protocol.

9. The method according to claim 8, wherein the expression data is analyzed for a genetic mutation.

10. The method according to claim 1, further comprising assigning the expression data to a specific transduced cell based on barcode identification.

11. The method according to claim 1, wherein the barcoded trans-splicing constructs further comprise an effector element.

12. The method according to claim 1, wherein the cellular sample is derived from a biological fluid sample, a tissue sample, or cells grown in vitro.

13. The method according to claim 12, wherein the target mammalian cell is a diseased cell.

14. The method according to claim 13, wherein the diseased cell is a circulating tumor cell.

15. The method according to claim 13, wherein after contacting the cellular sample with the library, the diseased cell is treated with a drug.

16. The method according to claim 1, wherein the trans-splicing element includes a regulatory sequence to enhance trans-splicing efficiency.

17. The method according to claim 1, wherein the trans-splicing element includes a pre-mRNA target binding domain.

18. The method according to claim 2, wherein the branchpoint comprises the nucleotide sequence YNYYRAY, where Y denotes a pyrimidine, N denotes any nucleotide and R denotes a purine.

19. A method of obtaining a single cell expression profile from a target mammalian cell, the method comprising:
   contacting a cellular sample comprising the target mammalian cell with a packaged viral barcoded trans-splicing library comprising a plurality of barcoded trans-splicing constructs under transduction conditions, wherein a barcoded trans-splicing construct comprises a trans-splicing element linked to a barcode element and the plurality of barcoded trans-splicing constructs comprises a set of constructs each having a distinct barcode element linked to a common trans-splicing element that is a spliceosome-recognized trans-splicing element comprising a splice donor site comprising the nucleotide sequence AGGURAGU, where R denotes a purine; and
   generating expression data from the resultant transduced target mammalian cell to obtain the single cell expression profile from the target mammalian cell, wherein the single cell expression profile comprises the expression level of 50 or more genes of interest.

20. A method of obtaining a single cell expression profile from a target mammalian cell, the method comprising:
   contacting a cellular sample comprising the target mammalian cell with a packaged viral barcoded trans-splicing library comprising a plurality of barcoded trans-splicing constructs under transduction conditions, wherein a barcoded trans-splicing construct comprises a trans-splicing element linked to a barcode element and the plurality of barcoded trans-splicing constructs comprises a set of constructs each having a distinct barcode element linked to a common trans-splicing element that is a spliceosome-recognized trans-splicing element comprising a splice donor site, wherein the trans-splicing element includes a regulatory sequence to facilitate trans-splicing in mammalian cells; and generating expression data from the resultant transduced target mammalian cell to obtain the single cell expression profile from the target mammalian cell, wherein the single cell expression profile comprises the expression level of 50 or more genes of interest.

* * * * *

SEQUENCE LISTING

```
<160> NUMBER OF SEQ ID NOS: 18

<210> SEQ ID NO 1
<211> LENGTH: 391
<212> TYPE: DNA
<213> ORGANISM: Artificial sequence
<220> FEATURE:
<223> OTHER INFORMATION: synthetic polynucleotide

<400> SEQUENCE: 1
actagtatta tgcccagtac atgaccttat gggactttcc tacttggcag tacatctacg      60
tattagtcat cgctattacc atggtgatgc ggttttggca gtacatcaat gggcgtggat     120
agcggtttga ctcacgggga tttccaagtc tccacccat tgacgtcaat gggagtttgt      180
tttggcacca aaatcaacgg gactttccaa aatgtcgtaa caactccgcc ccattgacgc     240
aaatgggcgg taggcgtgta cggtgggagg tttatataag cagagctcgt ttagtgaacc     300
gtcagatcgc ctggagacgc catccacgct gttttgacct ccatagaaga ttctagaaca     360
cgctagctag ctagacgcca ccatggtgtc t                                    391

<210> SEQ ID NO 2
<211> LENGTH: 248
<212> TYPE: DNA
<213> ORGANISM: Artificial sequence
<220> FEATURE:
<223> OTHER INFORMATION: synthetic polynucleotide

<400> SEQUENCE: 2
tctagaccgt actgaccctc ctctgtttcc ttttttttc acaggttcgg actgtagaac      60
tctgaacctc tccttgcgtg taggtctcgg tggtcgccgt atcattctgt cgtctcggtg     120
```

```
gtcgagatct ggcatgactg ggaggagaca aaggaaaaaa aaagtgtcca agcctgacat    180
cttgagactt ggagaggaac gcacatccag agccaccagc ggcatagtaa gacagcagag    240
ccaccagc                                                              248
```

<210> SEQ ID NO 3
<211> LENGTH: 199
<212> TYPE: DNA
<213> ORGANISM: Artificial sequence
<220> FEATURE:
<223> OTHER INFORMATION: synthetic polynucleotide

<400> SEQUENCE: 3

```
atcgcctgga gacgccatcc acgctgtttt gacctccata gaagattcta gaccgtactg     60
accctcctct gtttcctttt tttttcacag gttcggactg tagaactctg aacctctcct    120
tgcgtgtagg tctcggtggt cgccgtatca ttctgtcgtc tcggtggtcg ctagctagct    180
agacgccacc atggtgtct                                                  199
```

<210> SEQ ID NO 4
<211> LENGTH: 195
<212> TYPE: DNA
<213> ORGANISM: Artificial sequence
<220> FEATURE:
<223> OTHER INFORMATION: synthetic polynucleotide

<400> SEQUENCE: 4

```
tctagatcgc ctggagacgc catccacgct gttctgacct tgtttctttt tttttctgca     60
gagttgacgt cgggagaaga agctgttcat tttcagtgtg gatggtgtct ccaggtgata    120
ccggagtctt cttgaagaca cttcgtctgc gttgttctcg gtggtcgccg ttctgtcgtg    180
tcggtgctcg ctagc                                                      195
```

<210> SEQ ID NO 5
<211> LENGTH: 340
<212> TYPE: DNA
<213> ORGANISM: Artificial sequence
<220> FEATURE:
<223> OTHER INFORMATION: synthetic polynucleotide

<400> SEQUENCE: 5

```
ttcgaattaa ccgcagtaca tgaccttatg ggactttcct acttggcagt acatctacgt     60
attagtcatc gctattacca tcctgttgcg gttttggcag tacatcaatg ggcgtggata    120
gcggtttgac tcacggggat ttccaagtct ccacccatt gacgccaatg ggagtttgtt    180
ttggcaccaa aatcaacggg actttccaaa atgtcgtaac aactccgccc cattgacgca    240
aatgggcggt aggcgtgtac ggtggaaggt ttatataagc agagctcgtt tagtgaacct    300
ctagattttt gctagctagc tagacgccac catggtgtct                           340
```

<210> SEQ ID NO 6
<211> LENGTH: 148
<212> TYPE: DNA
<213> ORGANISM: Artificial sequence
<220> FEATURE:
<223> OTHER INFORMATION: synthetic polynucleotide

<400> SEQUENCE: 6

```
tctagatcgt actgactctg tttctttttt tttctgcaga gttgacgtcg ggagaagaag     60
ctgttcatac cggagtcttc ttattagaag acacttcgtc tgcgttgttc tcggtggtcg    120
```
ccgttctgtc gtgtcggtgc tcgctagc                                         148

<210> SEQ ID NO 7
<211> LENGTH: 171
<212> TYPE: DNA
<213> ORGANISM: Artificial sequence
<220> FEATURE:
<223> OTHER INFORMATION: synthetic polynucleotide

<400> SEQUENCE: 7
tctagattcc cggagacaca ctccgggaat tttctgacct tgtttctttt tttttctgca      60
gaccgatcct gctgaacaag acgactcgtc tgcttaccgg agtcttcttg aagacacttc     120
gtctgcgttg ttctcggtgg tcgccgttct gtcgtgtcgg tgctcgctag c              171

<210> SEQ ID NO 8
<211> LENGTH: 179
<212> TYPE: DNA
<213> ORGANISM: Artificial sequence
<220> FEATURE:
<223> OTHER INFORMATION: synthetic polynucleotide

<400> SEQUENCE: 8
tctagattcc cggagacaca ctccgggaat tttctgacct tgtttctttt tttttctgca      60
gaccgatcct gctgaacaag acgactcgtc tgcttaccgg agtcttcttg aagacactct     120
gcgttgttct cggtggtcgc cgttctgtcg tgtcggtgct cgatcaggta agtgctagc      179

<210> SEQ ID NO 9
<211> LENGTH: 174
<212> TYPE: DNA
<213> ORGANISM: Artificial sequence
<220> FEATURE:
<223> OTHER INFORMATION: synthetic polynucleotide

<400> SEQUENCE: 9
tctagattcc cggagacaca ctccgggaat tttctgacct tgtttctttt tttttctgca      60
gaccgatcct gctgaacaag acgactcgtc tgcttaccgg agtcttcttg aagacacagg     120
taagtctgcg ttgttctcgg tggtcgccgt tctgtcgtgt cggtgctcgc tagc           174

<210> SEQ ID NO 10
<211> LENGTH: 227
<212> TYPE: DNA
<213> ORGANISM: Artificial sequence
<220> FEATURE:
<223> OTHER INFORMATION: synthetic polynucleotide

<400> SEQUENCE: 10
tctagattcc cggagacaca ctccgggaat tttctgacct tgtttctttt tttttctgca      60
gaccgatcct gctgaacaag acgactcgtc tgcttaccgg agtcttcttg aagacactct     120
gcgttgttct cggtggtcgc cgttctgtcg tgtcggtgct cgatcaggta agttcataac     180
catctactaa ccgtcccctg tttcttcttt tctcacaggt tgctagc                   227

<210> SEQ ID NO 11
<211> LENGTH: 342
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t

<400> SEQUENCE: 11

```
tctagattcc cggagacaca ctccgggaat tttctgacct tgtttctttt tttttctgca    60
gaccgatcct gctgaacaag acgactcgtc tgcttacatc tagcggcctc tgtgtgaggc   120
ccttaaaaga ctggaacaaa gaaaaaaaaa gacgtctggc taggacgact tgttctgctg   180
agcagacgaa accghhhhhh hhhhhhchhh hnttcgtctg cgttgttctc ggtggtcgcc   240
gttctgtcgt gtcggtgctc gctagctggc ddddddddddd ddgddddnaa gcagacgcaa   300
caagagccac cagcggcaag acagcacagc cacgagcgat cg                      342
```

<210> SEQ ID NO 12
<211> LENGTH: 567
<212> TYPE: DNA
<213> ORGANISM: Artificial sequence
<220> FEATURE:
<223> OTHER INFORMATION: synthetic polynucleotide

<400> SEQUENCE: 12

```
attagtgaac ggatctcgac ggatttatcg atgttcgaat tctcctcgag ttttgcccct    60
cccccgtgcc ttccttgacc ctggaaggtg ccactcccac tgtcctttcc taataaaatg   120
aggaaattgc atcgcattgt ctgaataggt gtcattctat tctggggggt ggggtggggc   180
attcgaatta accgcagtac atgacccttat gggactttcc tacttcgcag tacatctacg   240
tattagtcat cgctattacc atgcagatgc ggttttcgca gtacatcaat gggcgtggat   300
agcgctttga ctcacgggga tttccaagtc tccaccccat tgacgccaat gggagtttgt   360
tttggcacca aaatcaacgg gactttccaa aatgtcgtaa caactccgcc ccattgacgc   420
aaatgggcgc taggcgtgta cggtggaagg tctatataag cagagctcgt ttagtgaacc   480
tctagattcg agtcttcttt tgaagacact tcgaaggtac ctttaagacc aatgacttac   540
aaggcagctg tagatcttag ccacttt                                       567
```

<210> SEQ ID NO 13
<211> LENGTH: 891
<212> TYPE: DNA
<213> ORGANISM: Artificial sequence
<220> FEATURE:
<223> OTHER INFORMATION: synthetic polynucleotide

<400> SEQUENCE: 13

```
atcgatcttt tttgtcgaat tcttttttaaa agaaaagggg ggattggggg gtacagtgca    60
ggggaaagaa tagtagacat aatagcaaca gacatacaaa ctaaagaatt acaaaaacaa   120
attacaaaaa ttcaaaattt ttctcgagtt ttgcccctcc ccgtgccttc cttgaccct    180
ggaaggtgcc actcccactg tcctttccta ataaaatgag gaaattgcat cgcattgtct   240
gaataggtgt cattctattc tggggggtgg ggtgggggcat tcgaatcgat cccacatcgc   300
ctgccactac ttaagtccga ttcacttcgg ctttagctcc aagcctttaa tctcgcgaag   360
ctctttttttt tttttaaca acataggagc tgtgattggc tgtttcagc caatcagcac   420
tgactcattt gcatagcctt tacaagcggt cacaaactca agaaacgagc ggttttaata   480
gtctttttaga atattgttta tcgaaccgaa taaggaactg tgcttgtga ttcacatatc   540
agtggagggg tgtggaaatg gcaccttgat ctcaccctca tcgaaagtgg agttgatgtc   600
```

| | |
|---|---|
| cttccctggc tcgctacaga cgcacttccg caagagtctt cttatgaaga ctcttcgtaa | 660 |
| ttttggagc aggttttctg acttcggtcg gaaaacccct cccaatttca ctggtctaca | 720 |
| atgaaagcaa aacagttctc ttccccgctc cccggtgtgt gagaggggct tgatccttc | 780 |
| tctggtttcc taggaaacgc gtatgtgcta gagccacgct ctgagacttc cgcctcgtgc | 840 |
| ggtcccgctt cctttctgcc tcctctggga attcggtacc tttaagacca a | 891 |

<210> SEQ ID NO 14
<211> LENGTH: 1134
<212> TYPE: DNA
<213> ORGANISM: Artificial sequence
<220> FEATURE:
<223> OTHER INFORMATION: synthetic polynucleotide

<400> SEQUENCE: 14

| | |
|---|---|
| attacgccaa gctctcgagg gccactccct ctctgcgcgc tcgctcgctc actgaggccg | 60 |
| ggcgaccaaa ggtcgcccga cgcccgggct tgcccgggc ggcctcagtg agcgagcgag | 120 |
| cgcgcagaga gggagtggcc aactccatca ctaggggttc ctggagggggt ggagtcgtga | 180 |
| atcgatgttc gaattctcct cgagttttgc ccctcccccg tgccttcctt gaccctggaa | 240 |
| ggtgccactc ccactgtcct ttcctaataa aatgaggaaa ttgcatcgca ttgtctgaat | 300 |
| aggtgtcatt ctattctggg gggtggggtg gggcattcga attaaccgca gtacatgacc | 360 |
| ttatgggact ttcctacttc gcagtacatc tacgtattag tcatcgctat taccatgcag | 420 |
| atgcggtttt cgcagtacat caatgggcgt ggatagcgct ttgactcacg ggatttcca | 480 |
| agtctccacc ccattgacgc caatgggagt tgttttggc accaaaatca acgggacttt | 540 |
| ccaaaatgtc gtaacaactc cgccccattg acgcaaatgg gcgctaggcg tgtacggtgg | 600 |
| aaggtctata taagcagagc tcgtttagtg aacctctaga ttcgagtctt cttttgaaga | 660 |
| cacttcgaag gtaccgcggc cgctaaggcc tcacctgcga tctcgatgct ttatttgtga | 720 |
| aatttgtgat gctattgctt tatttgtaac cattataagc tgcaataaac aaatggcgcc | 780 |
| ggcgatccgg agtggacgct agagctacga aataaacact ttaaacacta cgataacgaa | 840 |
| ataaacattg gtaatattcg acgttatttg ttgttaacaa caacaattgc attcatttta | 900 |
| tgtttcaggt tcaggggggag gtgtgggagg tttttttaaac tagtccactc cctctctgcg | 960 |
| cgctcgctcg ctcactgagg ccgggcgacc aaaggtcgcc cgacgcccgg gctttgcccg | 1020 |
| gcggcctca gtgagcgagc gagcgcgcag agagggactg cagaatactc tcgacaattc | 1080 |
| actggccgtc gttttacaac gtcgtgactg ggaaaaccct ggcgttaccc aact | 1134 |

<210> SEQ ID NO 15
<211> LENGTH: 1377
<212> TYPE: DNA
<213> ORGANISM: Artificial sequence
<220> FEATURE:
<223> OTHER INFORMATION: synthetic polynucleotide

<400> SEQUENCE: 15

| | |
|---|---|
| attacgccaa gctctcgagg gccactccct ctctgcgcgc tcgctcgctc actgaggccg | 60 |
| ggcgaccaaa ggtcgcccga cgcccgggct tgcccgggc ggcctcagtg agcgagcgag | 120 |
| cgcgcagaga gggagtggcc aactccatca ctaggggttc ctggaggggt ggagtcgtga | 180 |
| atcgattttt gccctccccc cgtgccttcc ttgaccctgg aaggtgccac tcccactgtc | 240 |
| ctttcctaat aaaatgagga aattgcatcg cattgtctga ataggtgtca ttctattctg | 300 |
| gggggtgggg tgggggcattc gaatcgatcc cacatcgcct gccactactt aagtccgatt | 360 |

```
cacttcggct ttagctccaa gcctttaatc tcgcgaagct ctttttttt ttttaacaac      420 ataggagctg tgattggctg ttttcagcca atcagcactg actcatttgc atagcctta      480 caagcggtca caaactcaag aaacgagcgg ttttaatagt cttttagaat attgtttatc      540
gaaccgaata aggaactgtg ctttgtgatt cacatatcag tggagggtg tggaaatggc      600 accttgatct caccctcatc gaaagtggag ttgatgtcct tccctggctc gctacagacg      660
cacttccgca agagtcttct tatgaagact cttcgtaatt tttggagcag ttttctgac      720 ttcggtcgga aaacccctcc caatttcact ggtctacaat gaaagcaaaa cagttctctt      780
ccccgctccc cggtgtgtga gaggggcttt gatccttctc tggtttccta ggaaacgcgt      840
atgtgctaga gccacgctct gagacttccg cctcgtgcgg tcccgcttcc tttctgcctc      900
ctctgggaat tcggtaccgc ggccgctaag gcctcacctg cgatctcgat gctttatttg      960
tgaaatttgt gatgctattg ctttatttgt aaccattata agctgcaata acaaatggc     1020 gccggcgatc cggagtggac gctagagcta cgaaataaac actttaaaca ctacgataac     1080
gaaataaaca ttggtaatat tcgacgttat ttgttgttaa caacaacaat tgcattcatt     1140
ttatgtttca ggttcagggg gaggtgtggg aggtttttta aactagtcca ctccctctct     1200
gcgcgctcgc tcgctcactg aggccgggcg accaaaggtc gcccgacgcc gggctttgc      1260 ccgggcggcc tcagtgagcg agcgagcgcg cagagaggga ctgcagaata ctctcgacaa     1320
ttcactggcc gtcgttttac aacgtcgtga ctgggaaaac cctggcgtta cccaact       1377
```

<210> SEQ ID NO 16
<211> LENGTH: 91
<212> TYPE: DNA
<213> ORGANISM: Artificial sequence
<220> FEATURE:
<223> OTHER INFORMATION: synthetic polynucleotide

<400> SEQUENCE: 16

```
gcaactgacc atgtttcttt ttttttctgc agacgaatcc tgctgaacaa gacgaacaac       60
accaccggag tcttcttatg aagactcttc g                                     91
```

<210> SEQ ID NO 17
<211> LENGTH: 178
<212> TYPE: DNA
<213> ORGANISM: Artificial sequence
<220> FEATURE:
<223> OTHER INFORMATION: synthetic polynucleotide

<400> SEQUENCE: 17

```
attcggatag aggatgtatc agatattact gaccatgttt ctttttttt ctgcagacga       60 atcctgctga acaagacgga cgaagaagcg gagacagcga cgaagaacaa caccaactga      120
cacacaacac acactgacca caattttga accggagtct tcttatgaag actcttcg        178
```

<210> SEQ ID NO 18
<211> LENGTH: 98
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (18)..(25)
<223> OTHER INFORMATION: n is a, c, g, or t

```
<220> FEATURE:
<221> NAME/KEY: misc_feature
<222> LOCATION: (30)..(37)
<223> OTHER INFORMATION: n is a, c, g, or t

<400> SEQUENCE: 18
ttcgcaggtc tccaccgnnn nnnnnttatn nnnnnnnttc gtctgcgttg ttctcggtgg      60
ttctgtcgtg tcggtgctcg ttcgtgagac cgcaggtt                             98
```